US009895428B2

(12) United States Patent
Broom et al.

(10) Patent No.: US 9,895,428 B2
(45) Date of Patent: Feb. 20, 2018

(54) METHODS OF TREATING ANTIBODY-MEDIATED REJECTION IN ORGAN TRANSPLANT PATIENTS WITH C1-ESTERASE INHIBITOR

(71) Applicant: SHIRE VIROPHARMA INCORPORATED, Lexington, MA (US)

(72) Inventors: Colin Broom, Devon, PA (US); Marc E. Uknis, Chadds Ford, PA (US)

(73) Assignee: Shire Viropharma Incorporated, Lexington, MA (US)

( * ) Notice: Subject to any disclaimer, the term of this patent is extended or adjusted under 35 U.S.C. 154(b) by 341 days.

(21) Appl. No.: 14/550,075

(22) Filed: Nov. 21, 2014

(65) Prior Publication Data
US 2015/0147319 A1 May 28, 2015

Related U.S. Application Data

(60) Provisional application No. 61/907,550, filed on Nov. 22, 2013, provisional application No. 62/029,086, filed on Jul. 25, 2014.

(51) Int. Cl.
| | |
|---|---|
| *A61K 38/57* | (2006.01) |
| *A61K 38/55* | (2006.01) |
| *A61K 35/16* | (2015.01) |
| *A61K 45/06* | (2006.01) |
| *C07K 16/00* | (2006.01) |
| *A61K 35/12* | (2015.01) |
| *A61K 39/00* | (2006.01) |

(52) U.S. Cl.
CPC .............. *A61K 38/57* (2013.01); *A61K 35/16* (2013.01); *A61K 38/55* (2013.01); *A61K 45/06* (2013.01); *C07K 16/00* (2013.01); *A61K 2035/122* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2002/0168352 A1 | 11/2002 | Winkler et al. | |
| 2009/0118162 A1 | 5/2009 | Shapiro et al. | |
| 2009/0220518 A1 | 9/2009 | Dinarello et al. | |
| 2016/0008442 A1* | 1/2016 | Spirig ................. | A61K 45/06 514/20.3 |

FOREIGN PATENT DOCUMENTS

| | | | |
|---|---|---|---|
| EP | 1 240 904 A2 | | 9/2002 |
| EP | 13158478.1 | * | 3/2013 |
| WO | 2013/041677 A1 | | 3/2013 |
| WO | 2014/145519 A2 | | 9/2014 |

OTHER PUBLICATIONS

Clinical Trial NCT01147302 (Oct. 22, 2010).*
Author Not Known, A Randomized Double-Blind Placebo-Controlled Pilot Study to Evaluate the Safety and Effect of CINRYZE (C1 Esterase Inhibitor [Human]) for the Treatment of Acute Antibody-Mediated Rejection in Recipients of Donor-Sensitized Kidney Transplants, ClinicalTrials.gov Archive, Retrieved from the Internet: https//clinicaltrials.gov/archive/NCT (2013).
Author Not Known, Recombinant Human C1 Inhibitor for the Treatment of Early Antibody-Mediated Rejection in Renal Transplantation, ClinicalTrials.gov, Retrieved from the Internet: https://www.clinicaltrials.gov/ct2/show/NCT01035593?term=amr+cl&rank=2, (2012).
Author Not Known, Safety & Tolerability of Berinert (C1 Inhibitor) Therapy to Prevent Reaction, ClinicalTrials.gov Archive, Retrieved from the Internet: https//clinicaltrials.gov/archive/NCT, (2013).
Cai, J. et al., Humoral theory of transplantation: some hot topics, British Medical Bulletin, 105:139-155 (2013).
Ensor, C. and Doligalski, C., Antibody Mediated Rejection of the Cardiac Allograft, Cardiac Transplantation, retrieved from the Internet: http://cdn.intechopen.com/pdfs-wm/28047.pdf, pp. 23-40 (2015).
International Search Report for PCT/US2014/066784, 5 pages (dated Feb. 11, 2015).
Montgomery et al., Human Plasma-Derived C1 Esterase Inhibitor for the Treatment of Acute Antibody Mediated Rejection in Kidney Transplantation, American Journal of Transplantation, 14(S3):129-130 (2014).
Tillou, X. et al., Recombinant human C1-inhibitor prevents acute antibody-mediated rejection in alloimmunized baboons, Kidney International, 78(2):152-159 (2010).
Wagner, E. et al., Therapeutic potential of complement modulation, Nature Reviews Drug Discovery, 9(1):1474-1776 (2010).
Written Opinion for PCT/US2014/066784, 10 pages (dated Feb. 11, 2015).
Akalin, E. et al., "Intravenous Immunoglobulin and Thymoglobulin Facilitate Kidney Transplantation in Complement-Dependent Cytotoxicity B-Cell and Flow Cytometry T- or B-Cell Crossmatch-Positive Patients", Transplantation, 76 (10): 1444-1447 (2003).
Amara, U. et al., "Interaction Between the Coagulation and Complement System", Adv. Exp. Med. Biol., 632: 71-79 (2008).
Beinrohr, L. et al., "C1, MBL-MASPs and C1-inhibitor: novel approaches for targeting complement-mediated inflammation", Trends in Molecular Medicine, 14: 511-521 (2008).
Benzaquen, L. R. et al., "Terminal Complement Proteins C5b-9 Release Basic Fibroblast Growth Factor and Platelet-derived Growth Factor from Endothelial Cells", J. Exp. Med., 179: 985-992 (1994).
Bryan, C. F. et al., "Long-Term Graft Survival is Improved in Cadaveric Renal Retransplantation by Flow Cytometric Crossmatching", Transplantation, 66: 1827-1832 (1998).
Caldwell, E. et al., "Heparin Binding and Augmentation of C1 Inhibitor Activity", Arch. Biochem. Biophys., 361(2): 15-222 (1999).

(Continued)

*Primary Examiner* — Phillip Gambel
(74) *Attorney, Agent, or Firm* — Choate, Hall & Stewart LLP; Charles E. Lyon; Nishat A. Shaikh

(57) ABSTRACT

A method and composition for treating or preventing antibody-mediated rejection (AMR) of a transplanted organ are provided.

27 Claims, 15 Drawing Sheets

(56) References Cited

OTHER PUBLICATIONS

Caliezi, C. et al., "C1-Esterase Inhibitor: An Anti-Inflammatory Agent and Its Potential Use in the Treatment of Diseases Other Than Hereditary Angioedema", Pharmacol. Rev., 52(1): 91-112 (2000).
Davis A. et al., "Biological Activities of C1 Inhibitor", Mol. Immunol., 45(16): 4057-4063 (2008).
Elham, A. et al., "Complement in organ transplantation", Curr. Opin. Organ Transplant., 15(4): 486-491 (2010).
German Federal Medical Council, "Drug commission of the German medical profession: serious thrombogenesis following Berinert HS", Ger. Med. J., 97(15): A-1016/B-864/C-812 (2000).
Glotz, D. et al., Desensitization and Subsequent Kidney Transplantation of Patients Using Intravenous Immunoglobulins (IVIg), Am. J. Transplant., 2(8): 758-760 (2002).
Glotz, D. et al., "Eculizumab Decreases Early Antibody-Mediated Rejection in Sensitized Deceased Donor Kidney Transplant Recipients", European Society for Organ Transplantation, Transplant International, 26 (Suppl. 2) (2013).
Hack, C.E. et al., "C1-inhibitor substitution therapy in septic shock and in the vascular leak syndrome induced by high doses of interleukin-2", Intensive Care Med., 19(Suppl 1): S19-S28 (1993).
Haririan, A. et al., "The Impact of C4d Pattern and Donor-Specific Antibody on Graft Survival in Recipients Requiring Indication Renal Allograft Biopsy", Am. J. Transplant., 9(12): 2758-2767 (2009).
Hecker, J. et al., "C1-Inhibitor for Prophylaxis of Xenograft Rejection After Pig to Cynomolgus Monkey Kidney Transplantation", Transplantation, 73(5): 688-694 (2002).
Hentjes, B. et al., "C1-esterase-inhibitor levels in patients with and without reperfusion injury following lung transplantation (LTx)", Ann. Hematol., 74: p. A157, Abstract #9 (1997).
Horstick, G. et al., "Application of C1-Esterase Inhibitor During Reperfusion of Ischemic Myocardium Dose-Related Beneficial Versus Detrimental Effects", Circulation, 104(25): 3125-3131 (2001).
Jordan, S. et al., "Utility of Intravenous Immune Globulin in Kidney Transplantation: Efficacy, Safety, and Cost Implications", Am. J. Transplant., 3(6): 653-664 (2003).
Jostkleigrewe, F. et al., "The role of C1-esterase inhibitor (C1-INH) in the therapy of septic shock following severe thermal trauma", Ann. Hematol., 74: p. A123, Abstract #257 (1997).
Kirschfink, M. et al., "C1 inhibitor in anti-inflammatory therapy: from animal experiment to clinical application", Molecular Immunology, 36: 225-232 (1999).
Lefaucheur, C. et al., "Clinical Relevance of Preformed HLA Donor-Specific Antibodies in Kidney Transplantation", Am. J. Transplant., 8(2): 324-331 (2008).
Levy, J. et al., "The therapeutic potential of a kallikrein inhibitor for treating hereditary angioedema", Expert Opin. Investig. Drugs., 15(9): 1077-1090 (2006).
Loupy, A. et al., "Outcome of Subclinical Antibody-Mediated Rejection in Kidney Transplant Recipients with Preformed Donor-Specific Antibodies", Am. J. Transplant., 9(11): 2561-2570 (2009).
Marsh, J. et al., "The Allogeneic T and B Cell Response is Strongly Dependent on Complement Components C3 and C4", Transplantation, 72(7): 1310-1318 (2001).
Mauiyyedi, S. et al., "Acute Humoral Rejection in Kidney Transplantation: II. Morphology, Immunopathology, and Pathologic Classification", J. Am. Soc. Nephrol, 13: 779-787 (2002).
Montgomery, R. et al., "Plasmapheresis and Intravenous Immune Globulin Provides Effective Rescue Therapy for Refractory Humoral Rejection and Allows Kidneys to be Successfully Transplanted into Cross-Math-Positive Recipients", Transplantation, 70(6): 887-895 (2000).
Montgomery, R. et al., "Transplanting patients with a positive donor-specific crossmatch: A single center's perspective", Pediatr. Transplant., 8(6): 535-542 (2004).
Montgomery, R., "Renal Transplantation Across HLA and ABO Antibody Barriers: Integrating Paired Donation into Desensitization Protocols", Am. J. Transplant., 10(3): 449-457 (2010).

Montgomery, R. et al., "Desensitization in HLA-Incompatible Kidney Recipients and Survival", N. Engl. J. Med., 365: 318-326 (2011).
Murata, K. et al., "Mechanisms of complement activation, C4d deposition, and their contribution to the pathogenesis of antibody-mediated rejection", Transplantation Reviews, 23: 139-150 (2009).
Nielsen, E. et al., "Effect of supraphysiologic levels of C1-inhibitor on the classical, lectin and alternative pathways of complement", Molecular Immunology, 44: 1819-1826 (2007).
Patel, R. et al., "Significance of the Positive Crossmatch Test in Kidney Transplantation", N. Engl. J. Med., 280(14): 735-739 (1969).
Poirier, N. et al., "Recombinant Human C1-Inhibitor Inhibits Cytotoxicity Induced by Allo- and Xenoantibodies", Transplantation Proceedings, 40: 581-583 (2008).
Puttarajappa, C. et al., "Antibody-Mediated Rejection in Kidney Transplantation: A Review", Journal of Transplantation (2012).
Racusen, L. et al., "The Banff 97 working classification of renal allograft pathology", Kidney International, 55: 713-723 (1999).
Rother, R. et al., "C5 Blockade with Conventional Immunosuppression Induces Long-Term Graft Survival in Presensitized Recipients", Am. J. Transplant., 8(6): 1129-1142 (2008).
Sis, B. et al., "Banff '09 Meeting Report: Antibody Mediated Graft Deterioration and Implementation of Banff Working Groups", Am. J. Transplantation, 10: 464-471 (2010).
Smith, R. et al., "Four Stages and Lack of Stable Accommodation in Chronic Alloantibody-Mediated Renal Allograft Rejection in Cynomolgus Monkeys", Am. J. Transplant., 8(8): 1662-1672 (2008).
Sonnenday, C.J. et al., "Preemptive Therapy with Plasmapheresis/Intravenous Immunoglobulin Allows Successful Live Donor Renal Transplantation in Patients with a Positive Cross-Match", Transplantation Proceedings, 34: 1614-1616 (2002).
Stegall, M. et al., "Terminal Complement Inhibition Decreases Early Acute Humoral Rejection in Sensitized Renal Transplant Recipients", Am. J. Transplant., 10: 39, Abstract #1 (2010).
Tenner, A. et al., "Activator-Bound C1 is Less Susceptible to Inactivation by C1 Inhibition than is Fluid-Phase C1", J. Immunol., 137(2): 625-630 (1986).
Tillou, X. et al., "Recombinant human C1-inhibitor prevents acute antibody-mediated rejection in alloimmunized baboons", Kidney International, 78: 152-159 (2010).
Van Doorn, M. et al., "A phase I study of recombinant human C1 inhibitor in asymptomatic patients with hereditary angioedema", J. Allergy. Clin. Immunol., 116(4): 876-883 (2005).
Vangerow, B. et al., "C1-Inhibitor for treatment of acute vascular xenograft rejection in cynomolgus recipients of h-DAF transgenic porcine kidneys", Xenotransplantation, 8: 266-272 (2001).
Wavamunno, M.D. et al., "Transplant Glomerulopathy: Ultrastructural Abnormalities Occur Early in Longitudinal Analysis of Protocol Biopsies", Am. J. Transplant., 7(12): 2757-2768 (2007).
Wolfe, R.A. et al., Trends in Organ Donation and Transplantation in the United States, 1999-2008, Am. J. Transplant., 10: 961-972 (2010).
Wouters, D. et al., "C1 inhibitor: just a serine protease inhibitor? New and old considerations on therapeutic applications of C1 inhibitor", Expert Opin. Biol. Ther., 8: 1225-1240 (2008).
Retrieved from the internet: URL:https://clinicaltrials.gov/archive/NCT01147302/2013_11_18, "A Randomized Double-Bind Placebo-Controlled Pilot Study to Evaluate the Safety and Effect of CINRYZE (C1 Esterase Inhibitor [Human]) for the Treatment of Acute Antibody-Mediated Rejection in Recipients of Donor-Sensitized Kidney Transplants", Nov. 18, 2013.
Montgomery, R. et al., "Human Plasma-Derived C1 Esterase Inhibitor for the Treatment of Acute Antibody Mediated Rejection in Kidney Transplantation", American Journal of Transplantation, Abstract #2252, 14(S3): 129-130 (2014).
Ensor, Christopher R. et al., "Antibody Mediated Rejection of the Cardiac Allograft", retrieved from the internet: URL: http://cdn.intechopen.com/pdfs-wm/28047.pdf, pp. 23-40 (2012).
Retrieved from the Internet: URL: https://clinicaltrials.gov/archive/NCT01134510/2013_10_10, Oct. 10, 2013.

(56) References Cited

OTHER PUBLICATIONS

Wagner, Eric et al., "Therapeutic potential of complement modulation", Nature Reviews Drug Discovery, 9(1): 43-56 (2010).
Retrieved from the Internet: URL: https://www.clinicaltrials.gov/ct2/show/NCT01035593?term=amr+c1&rank=2, "Recombinant Human C1 Inhibitor for the Treatment of Early Antibody-Mediated Rejection in Renal Transplantation", Feb. 15, 2012.
Tillou, Xavier et al., "Recombinant human C1-inhibitor prevents acute antibody-mediated rejection in alloimmunized baboons", Kidney International, 78: 152-159 (2010).
Cai, Junchao et al., "Humoral theory of transplantation: some hot topics", British Medical Bulletin, 105: 139-155 (2013).
International Search Report/Written Opinion issued in corresponding International Application No. PCT/US2014/066784, filed Nov. 21, 2014.

* cited by examiner

| Subject Number | Plasmapheresis day(s) | Plasmapheresis # day 1-20 | plasma replacement (days 1-20) | blood (days 1-20) | IVIg (days 1-20) | IVIg product |
|---|---|---|---|---|---|---|
| 2010102 | 2, 4, 6, 8, 10, 11, 12, 13-19 | 14 | 2 units FFP on days 11 and 13 | none | none | n/a |
| 2010104 | 2, 4, 6, 8, 9-15 | 11 | 2 units FFP on days 2, 9, 10 | 2 units PRBC on day 12 | none | n/a |
| 2010105 | 1, 2, 3, 5, 7 | 5 | 2 units FFP on days 2 and 3 | none | none | n/a |
| 2010106 | 2, 3, 4, 5, 7, 9, 10, 12 | 8 | 2 units FFP on days 2, 3, 4, 5 | none | none | n/a |
| 2010107 | 1, 2, 4, 6, 8, 12 | 6 | none | none | none | n/a |
| 2010108 | 2, 4, 6, 8, 11 | 5 | none | none | 6-7000 mg on days 2, 4, 6, 8, 11 | cytogam |
| 2010109 | 1, 3, 4, 5, 6, 7, 9, 12 | 8 | none | 1 unit PRBC on day 5 | 5000 mg on days 1, 3, 4, 5, 6, 7, 9 and 12 | cytogam |
| 2010110 | 1, 2, 3, 4, 6, 8, 9, 11, 13, 15, 18, 20 | 12 | 2 units FFP on days 1, 2, 3, 4, 9 | 1 unit PRBC on day 10 | 7000 mg on days 6, 11, 13, 15 | cytogam |
| 2010111 | 1, 2, 3, 4, 5, 6, 7, 8, 9, 10, 11, 12, 14, 16, 17, 19 | 16 | 2 units FFP on days 1 through12 daily | 1 unit PRBC on days 2, 8, 9 | 7000 mg on days 14, 16, 17, 19 and 21 | cytogam |
| 2010112 | 1, 2, 4, 5, 7, 9, 11, 12, 19 | 9 | 2 units FFP on days 1 and 2 | none | 9-10000 mg on days 1, 2 4, 5, 7, 9, 11, 12, 19, 20 | cyotgam |
| 2010113 | 2, 3, 5, 6, 8, 10, 11, 13, 15, 17 | 10 | 2 units FFP on days 2, 3, 5, 6 | none | 4000 mg on days 1 through 11 | cytogam |
| 2010114 | 1, 2, 3, 5, 6, 7, 9, 10, 11, 13, 14 | 11 | 2 units FFP on days 1, 2, 3, 5, 6, 7, 9, 10, 11, 13 | 1 unit PRBC on days 2, 3, 8, 9, 12 | 1,000 mg days 5, 6, 7, 9, 13, 15 and 50,000 mg days 11, 16, 17, 18, and 19 | 50,000 units of gamunex; 1000 mg of cytogam |
| 2010115 | 2, 3, 4, 5, 6, 7, 8, 9, 10, 11, 12, 14 | 12 | 2 units FFP on days 5, 6, 7, 8, 9, 10, 11 | 1 unit PRBC on days 1 and 10 | 6000 mg on days 2 through 12 and 15 | cytogam |
| 2010116 | 1, 2, 4, 6, 7, 9, 11, 13 | 8 | none | 1 unit PRBC on days 2 and 6 | 6000 mg on days 1, 7, 9, 11 and 13 | cytogam |
| 2010201 | n/a | 0 | none | none | none | n/a |
| 2010202 | n/a | 0 | none | none | 70 mg on days 1 and 2 | unspecified |
| 2010401 | 1, 3, 5, 7, 9, 11, 13 | 7 | none | none | none | n/a |
| 2010501 | 4, 6, 8, 12, 14, 16 | 6 | none | none | none | n/a |

Ave PLASMAPHERESIS DAYS / COHORT
CINRYZE = 9 days
Placebo = 7.44 days

Figure 3

Subjects Treated with Placebo

|  | Baseline Adjusted | | Unadjusted | |
| --- | --- | --- | --- | --- |
|  | C1 INH Antigen (U/mL) | C1 INH Functional (U/mL) | C1 INH Antigen (U/mL) | C1 INH Functional (U/mL) |
| 2010102 | 0 | 23 | 10.1 | 169 |
| 2010105 | 6 | 127 | 15 | 181 |
| 2010108 | 0 | 0 | 15 | 197 |
| 2010110 | 1.6 | 49 | 17 | 134 |
| 2010112 | 0 | 42 | 13.8 | 115 |
| 2010113 | 2.5 | 24 | 16.9 | 105 |
| 2010115 | 7 | 13 | 21.2 | 127 |

Subjects Treated with Cinryze®

|  | Baseline Adjusted | | Unadjusted | |
| --- | --- | --- | --- | --- |
|  | C1 INH Antigen (U/mL) | C1 INH Functional (U/mL) | C1 INH Antigen (U/mL) | C1 INH Functional (U/mL) |
| 2010104 | 7 | 78 | 17 | 164 |
| 2010106 | 8 | 129 | 16 | 185 |
| 2010107 | 9 | 180 | 14 | 202 |
| 2010109 | 15 | 105 | 27 | 191 |
| 2010111 | 6.8 | 87 | 22.5 | 173 |
| 2010114 | 3.9 | 73 | 20.7 | 169 |
| 2010116 | 6.6 | 44 | 22.9 | 166 |

Figure 8

METHODS OF TREATING ANTIBODY-MEDIATED REJECTION IN ORGAN TRANSPLANT PATIENTS WITH C1-ESTERASE INHIBITOR

CROSS-REFERENCE TO RELATED APPLICATIONS

This application claims the benefit of U.S. Provisional Application No. 61/907,550, filed Nov. 22, 2013, and U.S. Provisional Application No. 62/029,086, filed Jul. 25, 2014, the entirety of which are incorporated by reference herein.

FIELD OF THE INVENTION

The present invention relates generally to methods and compositions for treating organ transplant rejection in patients and more particularly but not exclusively to methods and pharmaceutical compositions for treating or preventing antibody-mediated rejection in organ transplant patients using a C1-esterase inhibitor.

BACKGROUND OF THE INVENTION

Each year patients are prohibited from receiving a potentially life-saving organ transplant because of a pre-existing antibody directed against the donor's cell surface human leukocyte antigens (HLA). Such patients are considered "sensitized" to their donor organ, which may be the result of previous transplantations, pregnancy, and/or blood transfusions. The presence of certain donor-specific antibodies (DSA) is a contraindication to transplantation regardless of other factors that may indicate a donor match. DSA presence may cause hyperacute (immediate) antibody-mediated rejection (AMR) of the donor organ post-transplantation and possible loss of the donated organ. Patients having DSA (i.e., sensitized patients) thus spend a significantly longer time waiting for an acceptable donor organ. Thus, sensitized patients face not one, but at least two hurdles to organ donation: (1) blood type compatibility, and (2) sensitization. Furthermore, some patients may develop antibodies to their donor organ after transplantation, and such DSA is termed "de novo." It is now known that a majority of patients that lose their transplant to chronic rejection do so as a result of de novo DSA.

At present, there are few treatment options available to sensitized patients with antibody mediated rejection. The treatments available include, for example, rituximab, and plasmapheresis with, or without, intravenous immunoglobulin (IVIg).

Although the treatments available show varying effectiveness for treating AMR initially, their effects become diminished and are not sustained in nearly half of patients. Thus, the long term effect of currently available treatments is poor and an enormous unmet need exists in the field for efficacious treatments of AMR and treatments and compositions that improve overall transplant survival for patients receiving cross-match positive organ transplants.

SUMMARY OF THE INVENTION

The present invention meets the needs in the field by providing methods and compositions for advantageously administering a C1-esterase inhibitor (C1-INH) protein to organ transplant patients who experience or are at risk of experiencing antibody-mediated rejection (AMR) of the transplanted organ.

In one aspect, the invention provides a method of treating AMR of an organ allograft in a patient in need thereof. The method includes early and/or short term duration administration of a therapeutically effective amount of a C1-INH, wherein the therapeutically effective amount of the C1-INH is sufficient to provide long-lasting therapeutic effect. The C1-INH may be a human plasma derived C1-INH, such as Cinryze®. Optionally, the method of the invention may include subjecting the patient to plasmapheresis for removing DSA. Early, short term treatment with C1-INH, which may be an adjunct to plasmapheresis, can reduce the rate of chronic organ allograft rejection compared to plasmapheresis alone.

In other embodiments, the method of the invention may comprise administering intravenous immunoglobulin (IVIg) and/or fresh frozen plasma. In a further embodiment, the method of the invention may comprise administering an anti-lymphocyte preparation, rituximab, eculizumab, bortezomib, or a combination thereof. In certain embodiments of the method of the invention, the patient is being or has been treated with other known therapies for treating hyper-acute and/or acute AMR.

Additionally, in the method of the invention the organ to be treated may be a solid organ. Moreover, the solid organ may be selected from the group consisting of kidney, pancreas, intestine, heart, lung, and liver. In certain embodiments, the organ is kidney.

In another aspect, the invention provides a pharmaceutical composition for treating or delaying the progression of AMR of an organ allograft in a patient in need thereof. The pharmaceutical composition may include a C1-INH; an additional biologically active agent, such as an anti-lymphocyte preparation, rituximab, eculizumab, immunoglobulin (Ig), and combinations thereof; and a pharmaceutically acceptable carrier medium.

In contrast to the treatments currently available in the art, the invention provides an efficacious early and/or short term duration therapy for treating AMR in transplant recipients, as well as patients awaiting or undergoing organ transplantation, that provides long-lasting therapeutic effect.

BRIEF DESCRIPTION OF THE DRAWINGS

The foregoing summary and the following detailed description of the exemplary embodiments of the present invention may be further understood when read in conjunction with the appended drawings, in which:

FIG. 3 is a table indicating the standards of care provided to subjects in an exemplary study following the course in FIG. 2 where, of 14 subjects, 7 where treated with placebo and 7 were treated with a C1-INH. As referred to therein: fresh frozen plasma (FFP) and packed red blood cell transfusion (PRBC).

FIG. 4A graphically demonstrates the mean plasma concentration of functional C1-INH after infusion with either Cinryze® or placebo over the course of 13 days in the exemplary study. FIG. 4B graphically demonstrates the mean plasma concentration of functional C1-INH after infusion with either Cinryze® or placebo on day 13 of the exemplary study. Both FIGS. 4A and 4B are corrected means for each cohort, such that baseline levels of C1-INH functional were subtracted.

FIG. 6A indicates a normal renal tissue slice at 6 months post-transplant in a patient treated with Cinryze® that is not displaying CG (one of the 6/7 patients). FIG. 6B indicates a renal tissue slice at 6 months post-transplant that indicates CG in a patient treated with placebo (one of the 3/7 patients).

FIG. 7A represents an exemplary normal EM image of a PTC. FIG. 7B represents an EM image of a PTC obtained at 6 months post-transplant demonstrating glomerulopathy an patient treated with placebo (one of the 3/7 patients). In FIG. 7A, CL=capillary lumen, E=epithelium, and BS=basement membrane.

FIG. 8 includes tables of measured C1-INH antigen and functional C1-INH levels in subjects at day 13 of an exemplary study where the subjects were treated with either placebo or C1-INH in addition to the standard of care (plasmapheresis and/or IVIg). The C1-INH antigen levels reported are based on a measurement of protein weight concentration with conversion to U/mL using the conversion factor of 0.067 U/ml=1 mg/1 dL.

FIGS. 9A and 9B graphically correlate the baseline corrected C1-INH antigen levels to CG in patients receiving placebo (FIG. 9A) and Cinryze® (FIG. 9B). FIGS. 9C and 9D graphically correlate the baseline corrected functional C1-INH levels to CG in patients receiving placebo (FIG. 9C) and Cinryze® (FIG. 9D). FIGS. 9E and 9F graphically correlate the unadjusted C1-INH antigen levels to CG in patients receiving placebo (FIG. 9E) and Cinryze® (FIG. 9F). FIGS. 9G and 9H graphically correlate the unadjusted functional C1-INH levels to CG in patients receiving placebo (FIG. 9G) and Cinryze® (FIG. 9H). The C1-INH antigen levels reported are based on a measurement of protein weight concentration with conversion to U/mL using the conversion factor of 0.067 U/ml=1 mg/1 dL.

DETAILED DESCRIPTION OF THE INVENTION

Figure 1:
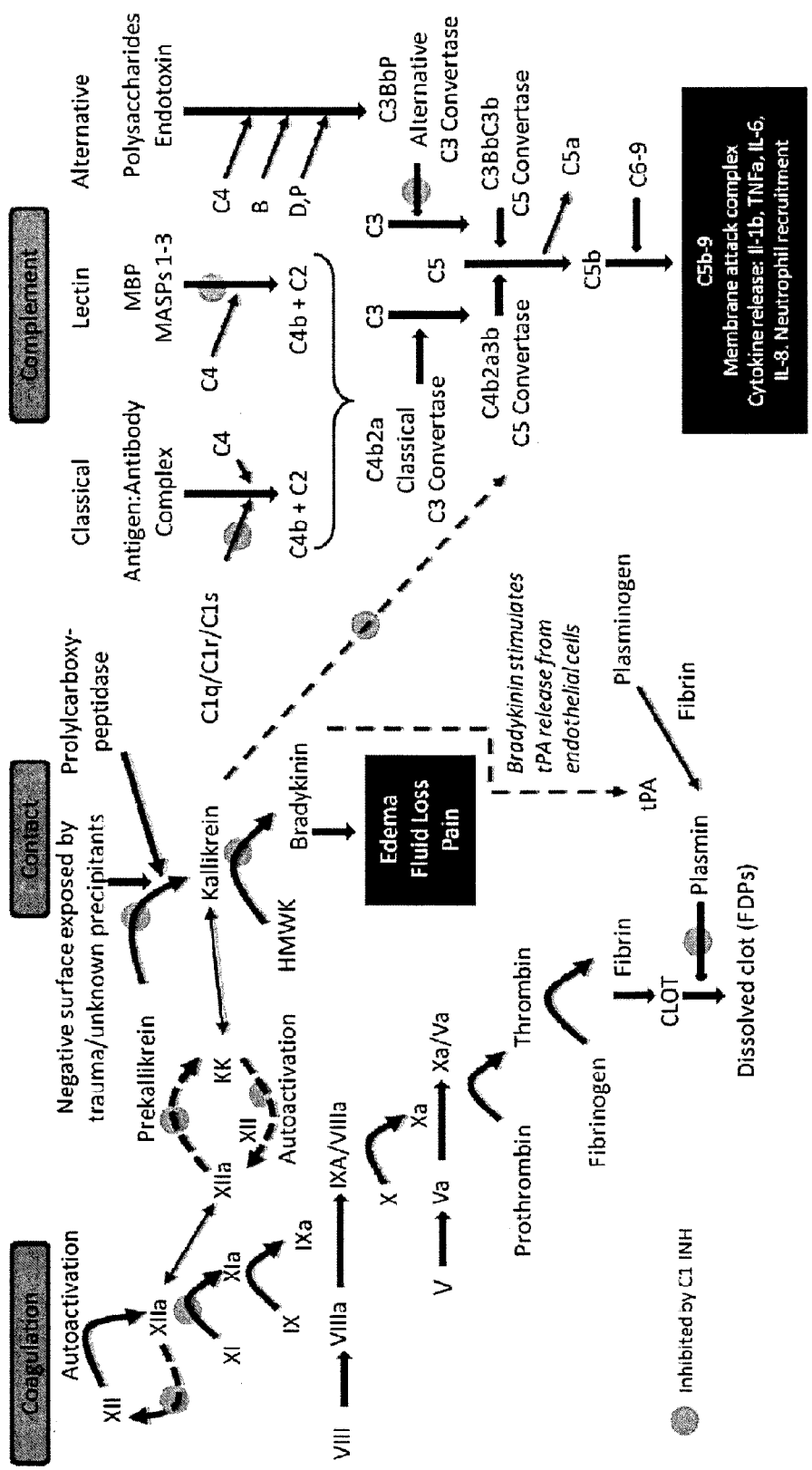
FIG. 1 schematically illustrates the effects of a C1-esterase inhibitor (C1-INH) on the coagulation, contact, and complement systems. As referred to therein: kallikrein (KK); high molecular weight kininogen (HMWK); mannose-binding protein (MBP); MBP-associated serine protease (MASP); tissue plasminogen activator (tPA); and fibrin degradation product (FDP).

Antibody-mediated rejection (AMR) is implicated in foiling the transplantation of, for example, heart, lung, liver, pancreas, intestine and kidney allografts in patients. Because there are few experimental and no approved therapies for antibody-mediated rejection (AMR) and outcomes for transplants are strictly monitored by the Centers for Medicare and Medicaid (CMS), patients awaiting organ transplants with DSA are generally prohibited by most transplant centers from receiving donor organs to which they are sensitized. For example, every year several thousand end-stage renal disease (ESRD) patients are prohibited from receiving a potentially life-saving kidney transplant because of a pre-existing antibody (DSA) directed against the donor's cell surface human leukocyte antigens (HLA).

The presence of these circulating DSA, identified through pre-transplant cross-match screening (complement-dependent cytotoxicity assay or flow cytometry), is a contraindication to transplantation. DSA can cause immediate, or "hyperacute," antibody-mediated rejection (AMR) resulting in complement-mediated destruction and ultimately, loss of the transplanted organ.

Nearly one third of individuals on the kidney transplant waiting list in the United States (US) have circulating antibodies directed against ≥10% of the population HLA. These sensitized patients spend a significantly longer time waiting for an acceptable kidney to which they are not sensitized (i.e., "cross-match negative") for transplantation as compared to non-sensitized patients. In the US, it is estimated that 6,000 ESRD (wait list) patients and an additional 3,500 new wait list registrants per year have a willing live donor but cannot be transplanted due to sensitization or blood type incompatibility. The inability to transplant sensitized patients with kidneys from willing live donors further increases the demand for deceased donor kidneys, and thus, increases wait times for all listed patients.

Accreditation of kidney transplant programs by the US Centers for Medicaid and Medicare Services (CMS) is based primarily on a specific center's outcomes meeting or exceeding national benchmarks for kidney transplantation (1-year graft survival rates of ~95%). When a program's death or graft failure rate exceeds 150% of expected rates, the program is cited for non-conformance and can lose CMS certification to perform kidney transplants (see 42 CFR Part 482, §482.80 and §482.82 [2007]). Therefore, there is an unwillingness to perform kidney transplants in highly sensitized or cross-match positive patients. These patients, many of whom have a willing live donor, unduly burden the deceased donor wait list and many will die waiting for a transplant. However, an agent that is a useful therapy and/or adjunct for desensitized patients in the prevention or treatment of acute AMR may help change paradigms in transplantation, not only permitting access to potentially life-saving transplants, but also decreasing the wait list competition for those without a potential living donor.

Decreasing DSA titers in cross-match positive or otherwise sensitized patients through the use of intravenous immunoglobulin (IVIg) or a combination of plasmapheresis and IVIg has allowed for "desensitization" and conversion to negative cross-match for successful kidney transplantation in some patients.

However, despite such protocols, more than 10% of patients will lose their graft immediately or very early after transplantation due to hyperacute rejection or aggressive acute AMR. Moreover, 30%-50% of patients will still experience acute AMR, most within the first 1 to 3 months post-transplantation. In fact, 1-year graft survival was 60%-70% in patients with DSA and AMR compared to approximately 95% in patients with no DSA. Nevertheless, for some patients, the morbidity and mortality rates associated with dialysis warrant the risks of cross-match positive kidney transplantation. There remains an unmet need to improve overall outcomes for these high risk (cross-match positive) transplant patients.

Acute AMR is routinely treated with additional IVIg and plasmapheresis. However, approximately half of the patients diagnosed with early acute AMR suffer irreversible damage to their renal allograft as evidenced by transplant glomerulopathy (TG), which is often associated with interstitial fibrosis, glomerulosclerosis, and fibrointimal thickening. TG is a subset of CG since TG refers to glomerulopathy occurring specifically in the transplanted organ. Treatments such as IVIg and/or plasmapheresis provided short-lived activity as opposed to long-lasting therapeutic effect because such treatments eventually lose their effectiveness. As used herein the term "short-lived activity" refers to the activity of a treatment type against AMR that remains effective only while receiving the interventional therapy. In contrast, the term "long-lasting therapeutic effect" refers to the activity of a treatment type against AMR that remains effective from greater than about 3 to 6 months after cessation of therapy.

Patients with the foregoing features of TG have greatly impaired graft survival compared with patients who have no evidence of TG on biopsy. Some patients with severe acute AMR may require salvage therapy inclusive of rituximab (anti-CD20 antibody) and/or bortezomib (proteasome inhibitor) with or without splenectomy as a last treatment option. There remains an enormous unmet need for an agent that effectively treats acute AMR (lessening the need for drastic measures such as splenectomy) and improves overall graft survival so that sensitized ESRD patients may be granted access to transplantation after desensitization for a positive cross-match.

Turning to the development of therapies that may overcome the failings in the field, improvement of current AMR therapies requires addressing the underlying host immune response that leads to DSA-mediated TG and eventual loss of the allograft. Plasmapheresis and IVIg can decrease DSA titers. However, their use may not address the tissue destruction that occurs as a result of complement activation. HLA-DSA complexes activate the classical pathway of the complement cascade, ultimately resulting in the formation of membrane attack complexes and continuous release of inflammatory cytokines. As evidence of the role of complement in graft destruction, accumulation of the 4th complement protein degradation product (C4d) along peritubular capillaries (PTC) is predictive of AMR and associated with poor allograft survival. After adjusting for risk factors commonly associated with graft failure, patients who require renal allograft biopsy for decreased kidney function and had DSA in their serum with C4d staining on biopsy have a risk of graft loss that is three times higher than patients without DSA or C4d staining on biopsy. Therefore, a complement inhibitor would prove a useful therapy and/or adjunct in the treatment of AMR.

Transplantation of a vascularized allograft involves exposure of the recipient to donor HLA. Processing and presentation of donor HLA determine the recipient's immune response to the transplanted allograft. If soluble donor antigen is presented and recognized by a recipient's CD4 T-lymphocytes, cytokine release (e.g., IL-2) will propagate a cytotoxic T-cell response resulting in acute cellular rejection. B-lymphocyte recognition of donor HLA results in propagation of a memory B-cell response and production of DSA. HLA-DSA complexes stimulate the classical pathway of the complement system resulting in antibody-mediated rejection (FIG. 1).

DSA can complex with the first component of the classical complement pathway (C1) resulting in activated C1q/r/s and C4, eventually resulting in the formation of membrane attack complexes (C5b-9) and inflammatory cytokine release. These cytokines (e.g., IL-2, IL-6, and others) summon neutrophils and other mediators (for example, platelet derived growth factor) to illicit a local inflammatory response that can lead to fibrosis (irreversible scarring) of tissues, endothelial response, and injury resulting in coagulation and thrombosis of capillaries and larger vessels within the graft. The extent and immediacy of the damage is dependent upon whether (and to what extent) the DSA is pre-existing.

Donor HLA recognition by pre-existing DSA (with activation of the classical complement pathway) results in immediate (hyperacute) or early (within 1-3 months—accelerated) loss of the transplanted allograft. Such pathology may be temporarily alleviated by pre-transplant desensitization protocols (e.g., plasmapheresis and/or IVIg) directed at amelioration of DSA, but providing only short-lived activity in approximately 50% of such patients.

Additionally, clinical evidence indicates that patients who require renal allograft biopsy for decreased kidney function and have DSA in their serum with C4d staining (evidence of complement activation) on renal allograft biopsy have a risk of graft loss three times higher than patients without DSA or C4d staining on biopsy. Data from animal models also support the role of complement in allograft rejection. In a study of allotransplantation in Cynomolgus monkeys, among animals with known DSA, 54% of monkeys with C4d present on histopathology developed TG, compared with a TG rate of only 4% in transplanted monkeys with no evidence of C4d on biopsy.

Terminal complement (C5b-9) proteins (the product of antibody mediated classical complement pathway activation) can elicit production of fibroblast and platelet-derived growth factors from endothelial cells, causing intimal fibrosis, a hallmark of irreversible kidney transplant rejection. A preclinical mouse model of sensitized kidney transplantation showed improved graft survival in animals receiving a C5 inhibitor as adjunctive immunosuppression. In a study of 16 sensitized human kidney transplant recipients given the anti-C5 monoclonal antibody eculizumab after transplantation, only 1/16 (6%) developed acute AMR within the first month after transplant compared with ~40% of historical controls. However, all had persistent C4d staining and 4/16 (25%) had significant changes consistent with TG/endothelial cell activation. Long term follow up revealed that nearly 50% of these patients had TG after cessation of therapy, not different than the historical control.

More proximal signalling components of the classical complement cascade may have a greater role in alloimmunity. For instance, mice deficient in complement protein C3 or C4 had impaired T-cell and B-cell alloimmune responses to major histocompatability complex disparate skin grafts, while C5-deficient mice did not exhibit an impaired alloimmune response. Accordingly, there is a greater theoretical efficacy of C1-INH over a C5 inhibiting agent for prevention or treatment of AMR. The present invention provides such a therapy, utilizing a C1-INH treatment that provides long-lasting therapeutic effect that meets the needs in the field.

The present invention relates to methods for treating antibody-mediated rejection (AMR) of an organ allograft in a patient in need thereof, where the method includes administering a therapeutically effective amount of a C1-esterase inhibitor (C1-INH). The organ allografts that may be preserved from rejection by the methods described herein include solid organs. Representative examples of solid organs include heart, liver, lung, pancreas, intestine, and kidney. In certain embodiments, the solid organ may be kidney. In the method of the invention, the organ transplantation includes allotransplantation. By way of explanation, allotransplantation differs substantially from xenotransplantation. Allotransplation involves transplantation of organs that are from the same species (human-to-human transplant). In contrast, xenotransplantation involves transplantation of organs that are from differing species (e.g., pig-to-human organ transplant). Those having ordinary skill in the relevant art would recognize that cessation of C1-INH therapy would result in immediate AMR in xenotransplantation. However, this is irrelevant in human allotransplantation as there is no cross species sensitization.

As used herein, the terms "treatment," "treating," and the like refer to means for obtaining a desired pharmacologic or physiologic effect, for example. The effect may be prophylactic in terms of completely or partially preventing a condition, appearance, disease, or symptom and/or may be therapeutic in terms of a partial or complete cure for a condition and/or adverse effect attributable to a condition or disease. Without being limited to any one theory of operation, the methods of the invention are believed prevent and/or treat AMR in organ transplants by inhibiting components of the complement system.

Additionally, the term "short term duration" as used with respect to treatment, refers to the duration of drug treatment activities which may advantageously occur from about 1 to 30 days. In certain aspects, the short term duration of treatment may be about 10 to 20 days. In a preferred aspect, the short term duration of treatment may be about 13 days.

The term "early" as used herein regarding treatment, refers to the timing of treatment that may advantageously occur or be initiated within 1 to 90 days of: (1) organ transplantation, (2) treatment with the standard of care (plasmapheresis and/or IVIg), and/or (3) diagnosis of AMR. In preferred aspects, the treatment may occur or be initiated in less than about 5 to 10 days.

"Chronic glomerulopathy" or "CG" is a clinical marker of AMR in an organ transplant patient and, as used herein, refers to deleterious manifestations found in renal tissue including, for example, glomerulsclerosis, glomerular basement membrane thickening and lamination, and/or ongoing inflammation of the glomeruli. Peritubular vasculitis may also be present.

The term "transplant glomerulopathy" or "TG" as used herein refers to chronic glomerulopathy (CG) that occurs in the transplant setting. TG and CG may used interchangeably to describe the invention.

C1 esterase inhibitor (C1-INH) is an endogenous plasma protein in the family of serine protease inhibitors (SERPINs) and has broad inhibitor activity in the complement, contact, and coagulation pathways. C1-INH inhibits the classical pathway of the complement system by binding C1r and C1s and inhibits the mannose-binding lectin-associated serine proteases in the lectin pathway. The C1-INH of the present invention may be a plasma derived C1-INH or may be recombinantly produced C1-INH. Preferably, the C1-INH of the invention is a plasma derived C1-INH.

The term "Units" or "U" as used herein refers to the measure of protein (C1 INH) material, that is normalized to physiologic levels in human (i.e. 1 U/mL of serum is physiologic). In the alternative, one (1) Unit denotes 240 μg of protein material unless otherwise indicated.

A nanofiltered plasma derived C1-INH (Cinryze®; Viropharma) is FDA approved for routine prophylaxis against angioedema attacks in adolescent and adult patients with hereditary angioedema (HAE), a disease characterized by constitutional deficiency or dysfunction of endogenous C1 esterase inhibitor.

Cinryze® is known to be well tolerated in humans via the experience in patients with HAE studied in randomized trials as well as in an extension trial. The most frequent adverse events reported at the doses used for HAE were headaches and nasopharyngitis. C1-INH is an ideal therapeutic, either alone or as part of a combination therapy or composition, for diseases that implicate, for example, the classical complement pathway (e.g., antibody-mediated diseases) and of the lectin pathway (e.g., ischemia reperfusion injury).

The term "effective amount," as used herein, refers to the quantity of a compound or composition that achieves a beneficial clinical outcome when the compound or composition is administered to a patient. For example, when a composition of the invention is administered to a patient with, for example, AMR, a "beneficial clinical outcome" includes increased and/or sustained renal function and/or an increase in the longevity of the patient's allograft (e.g., transplanted kidney). As used herein, the term "renal function" is defined with respect to the ability of a patient's kidneys to clear creatinine from the body. Thus, for example, a patient demonstrating increased renal function would present with certain creatinine clearance ability (mL/min) (i.e., baseline) and such creatinine clearance ability or renal function would increase in magnitude from the baseline during treatment and after treatment.

The term "isolated," as used herein in describing a material, for example, refers to material removed from its original environment (e.g., the natural environment if it is naturally occurring). For example, a naturally-occurring polypeptide (i.e., protein) present in a living animal is not isolated, but the same polypeptide, separated from some or all of the coexisting materials in the natural system, is isolated.

Moreover, the "polypeptides" or "proteins" used in practicing the present invention may be natural proteins, synthesized proteins, or may be preferably recombinant proteins. Further, the proteins described herein can be naturally purified products, or chemically synthesized products, or recombinant products from prokaryotic or eukaryotic hosts (e.g., bacteria, yeast, higher plant, insect, or mammalian cell). Such proteins can be glycosylated or non-glycosylated according to the different hosts used.

Turning to the recombinant proteins used in practicing the invention, the recombinant C1-INH (rC1-INH) proteins can be expressed or produced by conventional recombinant DNA technology, using a polynucleotide sequence specific to C1-INH as known in the art. Generally, such recombinant procedure comprises the following steps:

(1) transfecting or transforming the appropriate host cells with the polynucleotide or its variants encoding C1-INH protein of the invention or the vector containing the polynucleotide;

(2) culturing the host cells in an appropriate medium; and (3) isolating or purifying the protein from the medium or cells.

In practice, the agents of the invention may be administered as separate dosage units or formulated for administration together, according to procedures well known to those skilled in the art. See, for example, *Remington: The Science and Practice of Pharmacy*, 20$^{th}$ ed., A. Genaro et al., Lippencot, Williams & Wilkins, Baltimore, Md. (2000).

Suitable methods of introduction of compositions of the invention to a patient include but are not limited to intradermal, intramuscular, intraperitoneal, intravenous, subcutaneous, intranasal, intraocular, epidural, and oral routes. Moreover, compositions of the invention may be administered by infusion or bolus injection, by absorption through epithelial or mucocutaneous linings (e.g., oral mucosa, rectal, and intestinal mucosa, etc.). Administration may further be systemic or local. And administration can be acute or chronic (e.g., daily, weekly, monthly, etc.).

The orally administered dosage unit may be in the form of tablets, caplets, dragees, pills, semisolids, soft or hard gelatin capsules, aqueous or oily solutions, emulsions, suspensions or syrups. Representative examples of dosage forms for parenteral administration include injectable solutions or suspensions, suppositories, powder formulations, such as microcrystals or aerosol spray. The composition may also be incorporated into a conventional transdermal delivery system.

In the methods disclosed herein, the compositions of the invention may be administered at a dose in range from about 10 Units (U) of composition per kg body weight (U/kg) to about 250 U/kg. A dose of from about 25 to 150 U/kg, and preferably from about 50 to 125 U/kg per day or, preferably, every other day of treatment should be effective to produce the desired result. By way of example, a suitable dose for IV administration would include an initial intravenous infusion of about 100 U/kg on day 1, followed by 50 U/kg on day 3. The compounds used in the method of the invention may typically be administered from 1-4 times a day or every other day, so as to deliver the above-mentioned dosage regimen.

Additionally, dosage of the compositions of the invention may be expressed as an amount of compound or composition divided equally or unequally over a course of treatment. For example, a course of treatment may last from about 1 to 30 days and about 1,000 to 25,000 units (U) of composition may be administered in divided doses over that course of treatment. In certain aspects, about 5,000 to 20,000 Units of composition may be administered by IV in divided doses over 10 to 20 days or, preferably, 13 days. However, the exact regimen for administration of the compounds described herein will necessarily be dependent on the needs of the individual subject being treated, the type of treatment administered and the judgment of the attending medical specialist. As used herein, the terms "subject" and "patient" includes both humans and animals. As those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

Additionally, in the methods of the invention, compositions may be administered as an adjunct to plasmapheresis therapy and/or IVIg. For example, in an exemplary method of the invention a composition including C1-INH (e.g., Cinryze®) may be administered to a patient as 20,000 units provided in divided doses (each dose not exceeding about 100 U/kg) over 10 to 20 days as an adjunct to plasmapheresis and/or IVIg. Such treatment may reduce the rate of chronic AMR at 3-6 months after cessation of therapy.

In certain situations, compounds (e.g., C1-INH) used in practicing the invention may be delivered as pharmaceutical compositions that include a pharmaceutically acceptable carrier medium. For example, the invention includes a pharmaceutical composition for treating or delaying the progression of antibody-mediated rejection (AMR) of an organ allograft in a patient in need thereof, the composition including a C1-esterase inhibitor (C1-INH); an additional biologically active agent, such as an anti-lymphocyte preparation, rituximab, bortezomib, eculizumab, immunoglobulin (Ig), or a combination thereof; and a pharmaceutically acceptable carrier medium.

As used herein, the expression "pharmaceutically acceptable carrier medium" includes any and all solvents, diluents, or other liquid vehicle, dispersion or suspension aids, surface agent agents, isotonic agents, thickening or emulsifying agents, preservatives, solid binders, lubricants, fillers and the like as suited for the particular dosage form desired. Remington: The Science and Practice of Pharmacy, 20th edition, A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. Except insofar as any conventional pharmaceutical carrier medium is incompatible with the compositions described herein, such as by producing an undesirable biological effect or otherwise interacting in an deleterious manner with any other component(s) of a formulation comprising the active agent(s), its use is contemplated to be within the scope of this invention.

More specifically, in the production of solid dosage forms the pharmaceutical composition may be mixed with pharmaceutically inert, inorganic or organic excipients, such as lactose, sucrose, glucose, gelatine, malt, silica gel, starch or derivatives thereof, talc, stearic acid or its salts, dried skim milk, vegetable, petroleum, animal or synthetic oils, wax, fat, polyols, and the like. Liquid solutions, emulsions or suspensions or syrups one may use excipients such as water, alcohols, aqueous saline, aqueous dextrose, polyols, glycerine, lipids, phospholipids, cyclodextrins, vegetable, petroleum, animal or synthetic oils. Suppositories may include excipients, such as vegetable, petroleum, animal or synthetic oils, wax, fat and polyols. Aerosol formulations may include compressed gases suitable for this purpose, such as oxygen, nitrogen and carbon dioxide. The pharmaceutical composition or formulation may also contain one or more additives including, without limitation, preservatives, stabilizers, e.g., UV stabilizers, emulsifiers, sweeteners, salts to adjust the osmotic pressure, buffers, coating materials and antioxidants.

The present invention further provides controlled-release, sustained-release, or extended-release therapeutic dosage forms for the pharmaceutical composition, in which the composition is incorporated into a delivery system. This dosage form controls release of the active agent(s) in such a manner that an effective concentration of the active agent(s) in the bloodstream can be maintained over an extended period of time, with the concentration in the blood remaining relatively constant, to improve therapeutic results and/or minimize side effects. Additionally, a controlled-release system would provide minimum peak to trough fluctuations in blood plasma levels of the active agent of the invention.

Additionally, various delivery systems are known and can be used to administer compositions that comprise C1-INH, or C1-INH in combination with a biologically active agent, such as immunoglobulin (Ig), rituximab, bortezomib and/or eculizumab, for example. Additionally, such compositions may, for example, be encapsulated in liposomes, microparticles, and microcapsules, for example.

The methods of the present invention will normally include medical follow-up to determine the therapeutic or prophylactic effect brought about in the patient undergoing treatment with the compound(s) and/or composition(s) described herein.

The results of the experiments described in the following example demonstrate that commercially available plasma-derived C1-INH can treat or prevent organ transplant rejection in patients exhibiting AMR. This example is provided for illustrative purposes only and is not intended to limit the invention in any way.

EXAMPLES

A randomized, double-blind, placebo-controlled pilot study was used to evaluate the safety and effect of Cinryze® (C1 esterase inhibitor [human]) for the treatment of acute antibody-mediated rejection in recipients of donor-sensitized kidney transplants. The objectives of the study were: (a) to assess the safety and tolerability of Cinryze® in kidney transplant patients with acute antibody-mediated rejection (AMR); (b) to assess the effect of Cinryze® for the treatment of acute AMR in kidney transplant patients; and (c) to examine the pharmacokinetics and pharmacodynamics of Cinryze® in kidney transplant patients with acute AMR.

In the present study, there were no discontinuations of treatment, no deaths, and no study drug related serious adverse events.

Cinryze® was supplied as a lyophilized powder of 500 U (C1-INH)/vial. Cinryze® product and sterile water for injection approved for commercial distribution were utilized. Each vial of Cinryze® was reconstituted with sterile water for injection(s). Placebo consisted of 0.9% sodium chloride for infusion.

Dosing.

Subjects received a total of 7 doses of study drug (Cinryze® or placebo) over a 2-week period (FIG. 2): an initial intravenous (IV) infusion of 5000 U Cinryze® (not to exceed 100 U/kg) or placebo on Day 1, followed by 2500 U of Cinryze® (not to exceed 50 U/kg) or placebo IV on Days 3, 5, 7, 9, 11, and 13. If plasmapheresis therapy occurred on the same day as study drug dosing, study drug was administered after completion of the plasmapheresis session.

Study Design.

Figure 2:
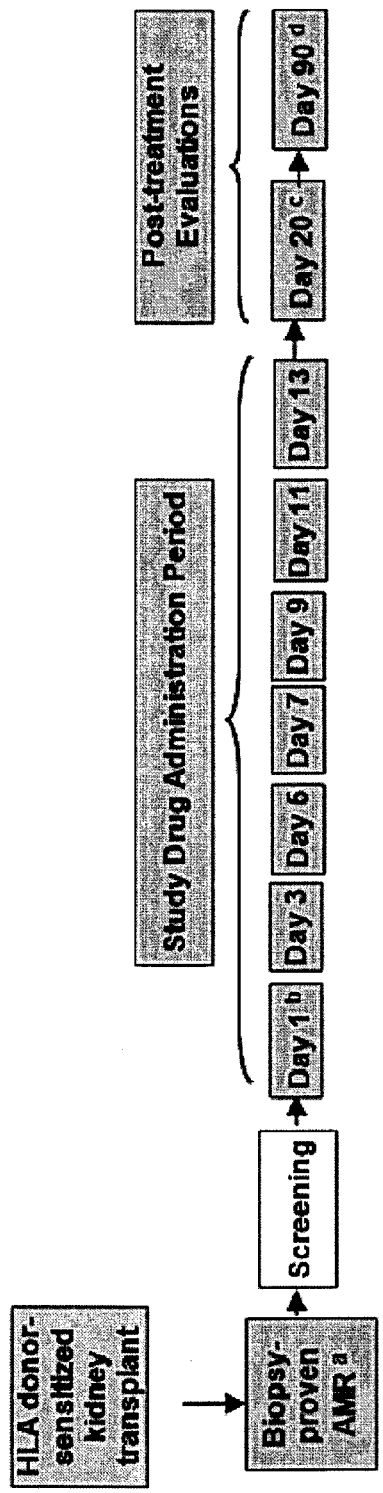
FIG. 2 diagrammatically illustrates an exemplary design for C1-INH inhibitor dosing using Cinryze® as the C1-INH. As referred to therein: (a) biopsy-proven AMR within 12 months after transplant; (b) first dose of either Cinryze® or placebo within 72 hours after qualifying biopsy; (c) day 20 (±24 hours) after first dose of either Cinryze® or placebo; and (d) day 90 (±24 hours) after first dose of either Cinryze® or placebo.

The study assessed the safety and effect of Cinryze® in the treatment of acute AMR in HLA donor-sensitized kidney transplant recipients (FIG. 2). To minimize variability, the study was conducted only at institutions that use plasmapheresis and/or intravenous immunoglobulin (IVIg), if necessary, for desensitization of DSA positivity and treatment of acute AMR. Subjects of the study had a kidney transplant that achieved adequate post-transplant function and a first ("qualifying") episode of biopsy-proven AMR with concurrent DSA identified prior to or after the most current renal allograft.

As illustrated in FIG. 2, post-treatment evaluations were performed on Day 20 and Day 90. The end of the study was defined as the date that the last subject completed the Day 90 evaluation. Complement and C1-INH levels were assessed at specified time points up to Day 20 for PK/PD determinations. In addition, an optional PK/PD sampling time point was included for Day 25. Additionally, at 6 months post-treatment an additional evaluation was provided from 14 equally randomized subjects (n=7 placebo; n=7 Cinryze®) treated similarly at a single transplant center to determine clinical outcome.

Study Drug Administration.

Based on available preclinical and clinical data, the physiologic levels of C1-INH sufficient for complement pathway inhibition elicited by antigen-antibody complexes are at least 100% above normal values. Following IV administration of 2000 U of Cinryze® in healthy subjects, the mean change from baseline in functional C1-INH activity was approximately 50-60%. Given that 1 U of C1-INH activity is found in 1 mL of plasma, to increase the functional activity of C1-INH by at least 100% in patients with acute AMR, a dose of about 5000 U may be required in an average adult. Given that Cinryze® has a half-life of about 60 hours in HAE patients, subsequent doses of 2500 U given every other day may maintain adequate functional C1-INH levels throughout the dosing period. Therefore, subjects randomized to the Cinryze® group in this study will receive a loading dose of 5000 U (not to exceed 100 U/kg) followed by 2500 U (not to exceed 50 U/kg) every other day for a total of 7 doses. This regimen balances the apparent dose-dependent nature of inhibiting complement activation elicited by antigen-antibody complexes, while minimizing the potential risk of coagulation observed in preclinical and clinical studies with other C1-INH compounds at doses ≥200 U/kg.

As set forth above, a total of 7 doses of Cinryze® or placebo (0.9% sodium chloride solution for infusion) were administered as follows: (a) an initial dose of 5000 U of Cinryze® (not to exceed 100 U/kg) or placebo as a single IV infusion on Day 1; and then (b) 2500 U of Cinryze® (not to exceed 50 U/kg) or placebo IV every other day for 2 weeks (Days 3, 5, 7, 9, 11, and 13). Each dose of study drug was to be administered IV at a rate of approximately 1 mL (corresponding to 100 U of Cinryze®) per minute as tolerated. Therefore, the duration of the 5000 U (50 mL) infusion on Day 1 was to be approximately 50 minutes and the duration of the 2500 U (25 mL) infusions on Days 3, 5, 7, 9, 11, and 13 was to be approximately 25 minutes. The 'start' and 'stop' times and dates of each study drug infusion was to be recorded.

Plasmapheresis, Fresh Frozen Plasma, and IVIg.

Plasmapheresis therapy was to be performed for the qualifying episode of AMR. Regardless of plasmapheresis schedule, study drug was to be administered on Days 1, 3, 5, 7, 9, 11, and 13. Moreover, as demonstrated in FIG. 3, certain patients were provided with, as necessary, the standard of care that included plasmapheresis, plasma replacement in the form of fresh frozen plasma (FFP), blood, and/or IVIg (e.g., cytogam, gamunex, etc.).

Pharmacokinetics/Pharmacodynamics.

Figure 4A:
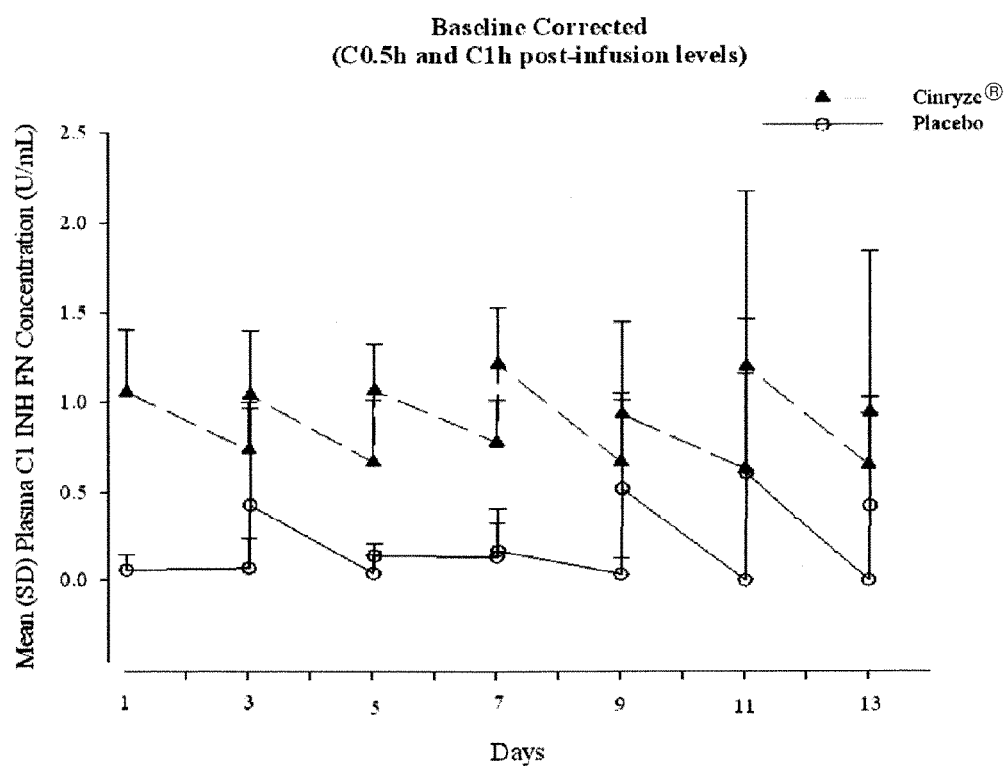
FIGS. 4A and 4B are graphs illustrating functional C1-INH plasma concentration levels (cohort means) in treated patients after infusion with either Cinryze® or placebo.
Figure 4B:
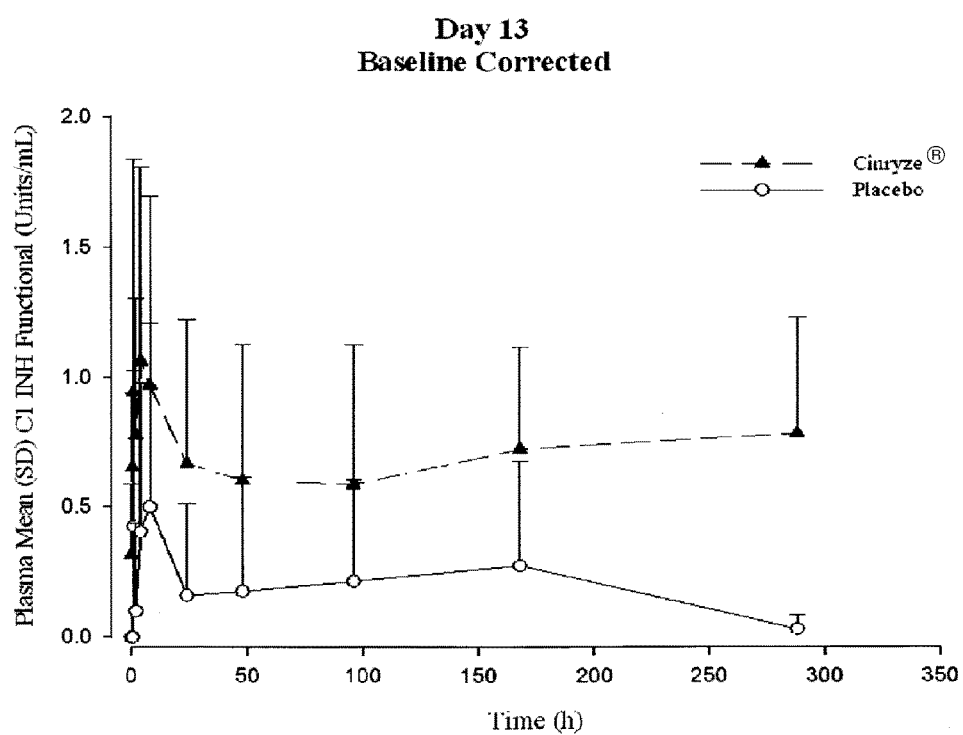

In the present study, an analysis of the pharmacokinetics and pharmacodynamics of Cinryze® were undertaken with respect to placebo. With respect to pharmacokinetic analyses, C1-INH antigen and functional levels for individual subjects were determined Primary PK parameters were calculated using baseline-corrected concentration-versus-time data following the last dose (Day 13) and noncompartmental techniques, as appropriate. Levels of C1-INH functional were analyzed in patients receiving C1-INH or placebo over the entire treatment time course (FIG. 4A). As expected, the cohort mean amount of C1-INH functional corrected for baseline levels was greater in patients receiving C1-INH (Cinryze®) on days 3, 5, 7, 9, 11, and 13. Additionally, the difference in mean baseline corrected plasma concentration of C1-INH functional is apparent at day 13 when the concentration was measured over a shorter time course (FIG. 4B). Thus, in patients treated with Cinryze® and plasmapheresis (and/or IVIg), there was a greater concentration of C1-INH functional (i.e., active classical complement pathway inhibitor protease) when compared to placebo (i.e., plasmapheresis (and/or IVIg) alone).

With respect to pharmacodynamic analyses, complement C1q, C4, and C4a levels for individual subjects were evaluated. Blood samples for the determination of plasma concentrations of C1-INH functional and antigenic and complement components C1q, C4, and C4a were collected (Table 1). If plasmapheresis was to be performed on a dosing day, blood samples for PK/PD testing was to be obtained before plasmapheresis, as well as prior to study drug administration (i.e., post-plasmapheresis), and at time points relative to the start of the study drug infusion.

TABLE 1

Study of the Pharmacokinetic and Pharmacodynamic effects of Cinryze ® with respect to Placebo

|  | Cinryze ® | Placebo |
|---|---|---|
| Antigen (U/mL) | 0.477 | 0.118 |
| Function (U/mL) | 0.994 | 0.309 |
| C1q (µg/mL) | 37.9 | 17.2 |
| C4 (ng/mL) | 113 | 70 |
| C4a (ng/mL) | 55 | 400 |

With respect to Table 1, Cinryze® patients exhibited increased C1-INH functional and classical complement system inhibition where baseline levels were subtracted for calculation of the mean to demonstrate the overall effect of study drug therapy in each cohort. Compared to placebo, Cinryze® patients demonstrated increased levels (above baseline entry levels) of both C1-INH antigenic and functional in plasma, indicating a greater concentration of active and total C1-INH beyond the levels which patients began their study dosing. The C1-INH antigen levels reported are based on a measurement of protein weight concentration with conversion to U/mL using the conversion factor of 0.067 U/ml=1 mg/1 dL (unless otherwise indicated). In fact the unadjusted range (where baseline levels were not subtracted) for C1-INH functional was 1.59-2.02 U/mL at the end of Cinryze® therapy. However, this was not statistically different than the unadjusted range for placebo treated patients. Nevertheless, there was a noticeable cohort difference when examined for C1-INH above their entry level.

Cinryze® patients exhibited evidence of systemic inhibition of the complement system in the fluid phase. Patients treated with Cinryze® exhibited an increased plasma concentration (corrected for baseline entry levels) of C1q and C4, which are classical complement pathway proteins that would show a decreased concentration in plasma if the classical complement pathway were uninhibited. However, since the concentration of C1q and C4 is increased, this indicates some level of systemic inhibition.

Finally, classical complement pathway inhibition is confirmed by the decreased plasma concentration of C4a as compared to placebo. Ordinarily, upon complement system activation C4 is converted to C4a, thereby reducing the plasma concentration of C4. The present analysis indicates that in patients treated with additional exogenous C1-INH (Cinryze®) exhibited an increase in C1-INH functional protein that apparently led to systemic complement system inhibition.

Figure 5:
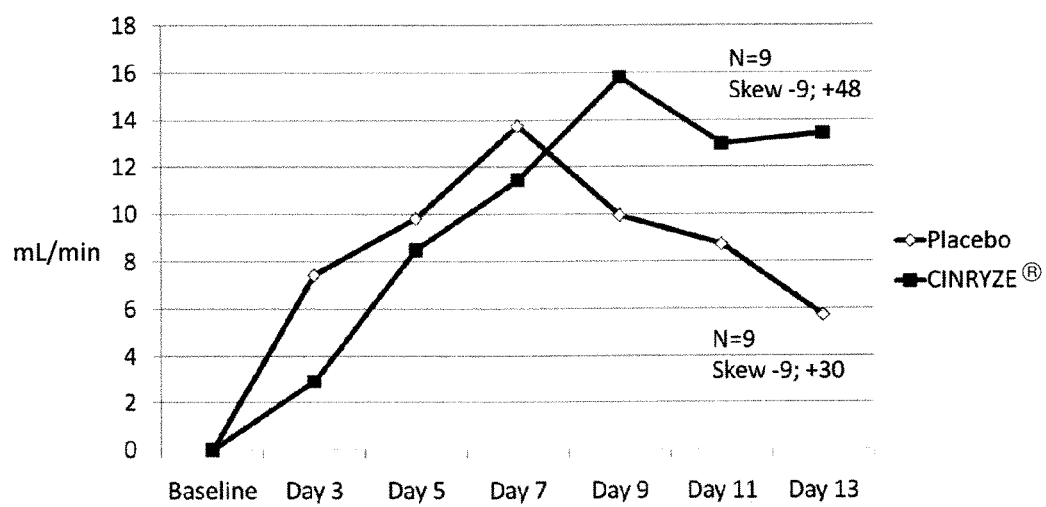
FIG. 5 graphically represents the mean change in renal function (i.e., creatinine clearance) in patients treated with either Cinryze® or placebo. Creatinine clearance is greatly reduced in AMR patients. By administering Cinryze®, as compared to placebo, the creatinine clearance is stabilized after approximately 7 days and does not drop off to the same degree as those patients treated with placebo. However, it is noted that the patients in the exemplary study are treated with plasmapheresis (and/or IVIg) and either Cinryze® or placebo.

In examining the physiological effects of C1-INH treatment, FIG. 5 discloses differences in mean renal function (i.e., creatinine clearance) between the cohort of patients treated with Cinryze® or placebo in combination with plasmapheresis (and/or IVIg) over the 13 day time course.

Figure 6A:
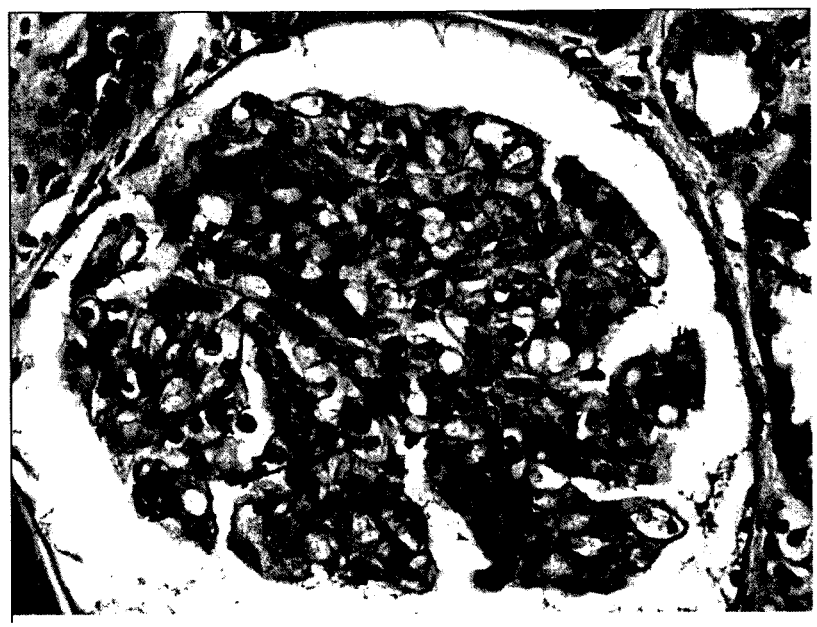
FIGS. 6A and 6B display renal tissue slices stained with hematoxylin and eosin (H&E) stain that illustrate and contrast the presence of chronic glomerulopathy (CG).
Figure 6B:
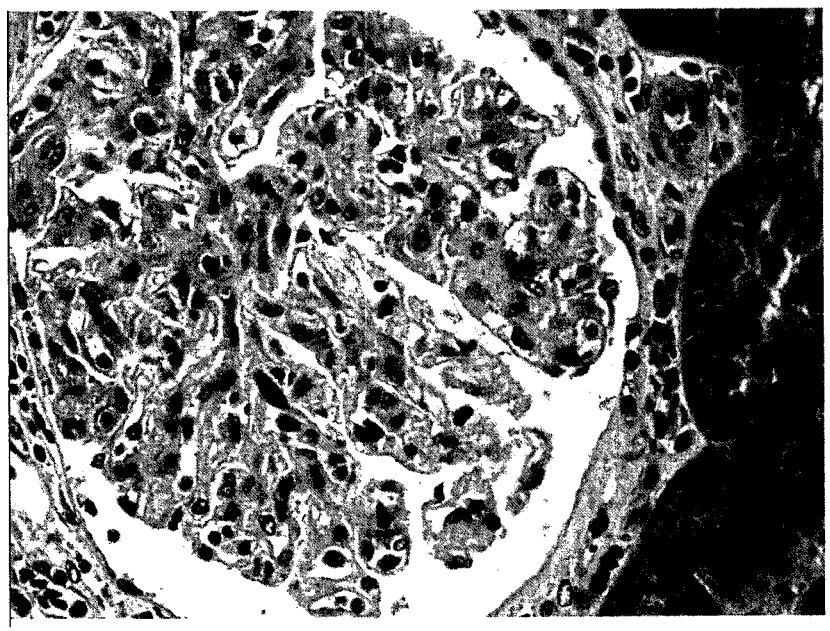
Figure 7A:
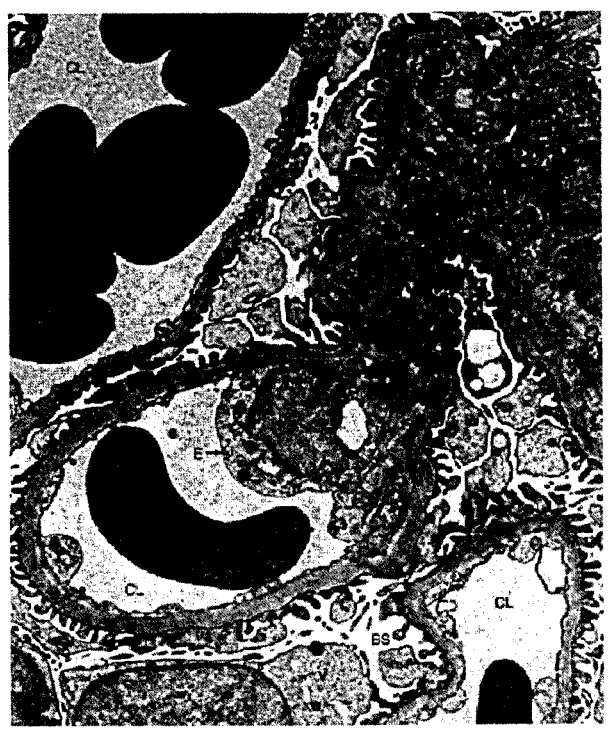
FIGS. 7A and 7B provide electron microscopy (EM) images of peritubual capillaries (PTC).
Figure 7B:
Figure 9A:
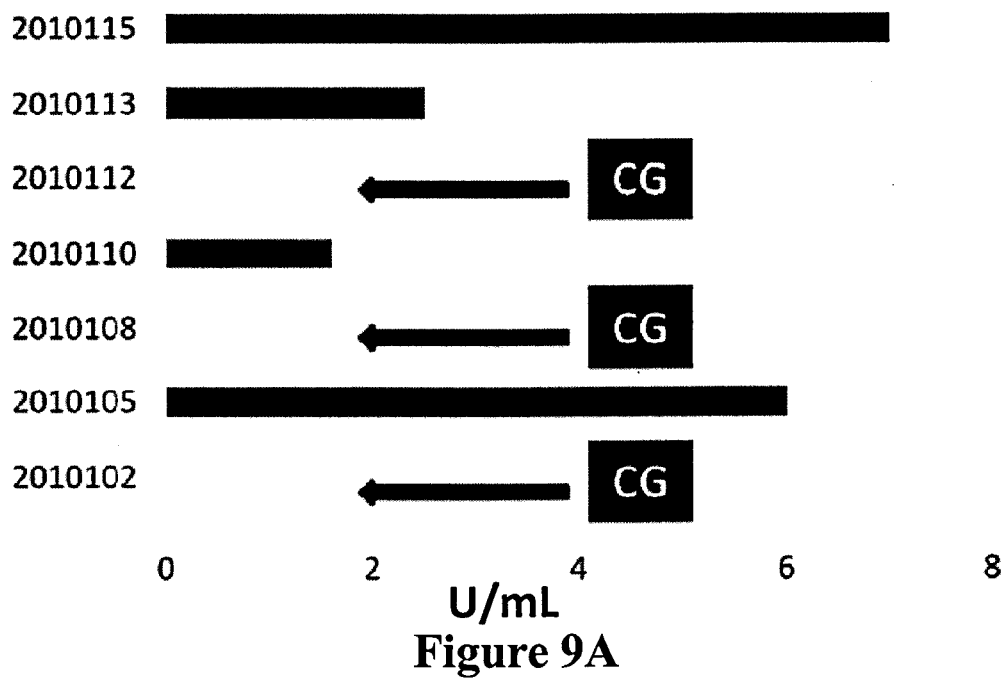
FIGS. 9A to 9H graphically correlate the levels of C1-INH antigen and functional C1-INH measured in patients at day 13 of the exemplary study (FIG. 8) with respect to their 6 month clinical outcome. As used therein: CG indicates those patients that had poor outcomes (e.g., 3/7 patients in placebo cohort, 1/patients in Cinryze® cohort); Antigen (AG); and functional (Fnct). Additionally, the one patient of the Cinryze® cohort who displayed CG had an adverse event of hemorrhagic shock after a biopsy while receiving anti-coagulation medicine.
Figure 9B:
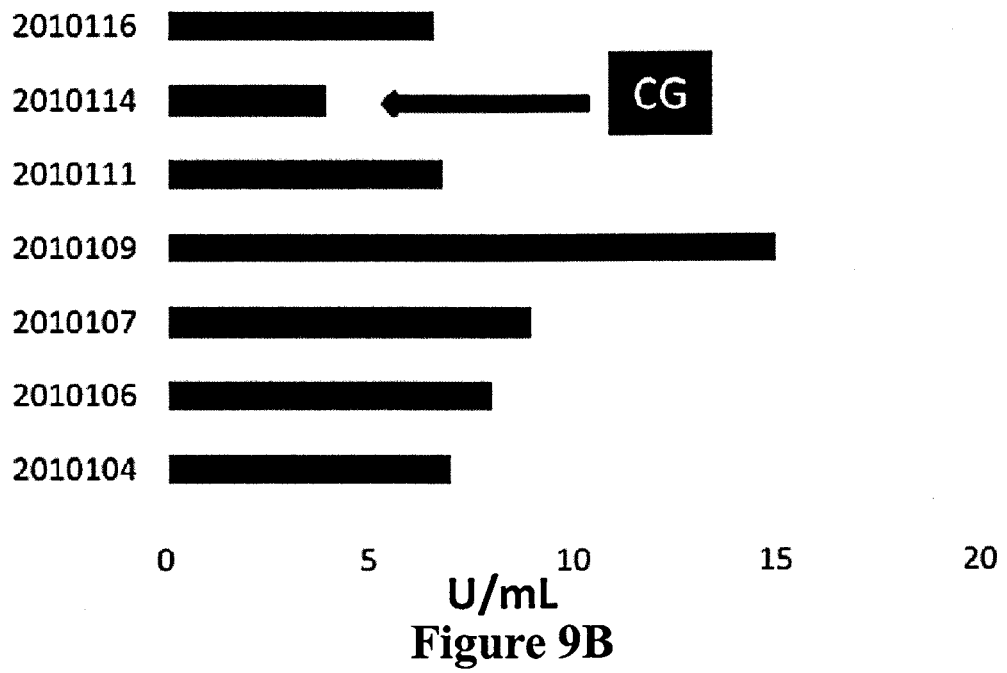
Figure 9C:
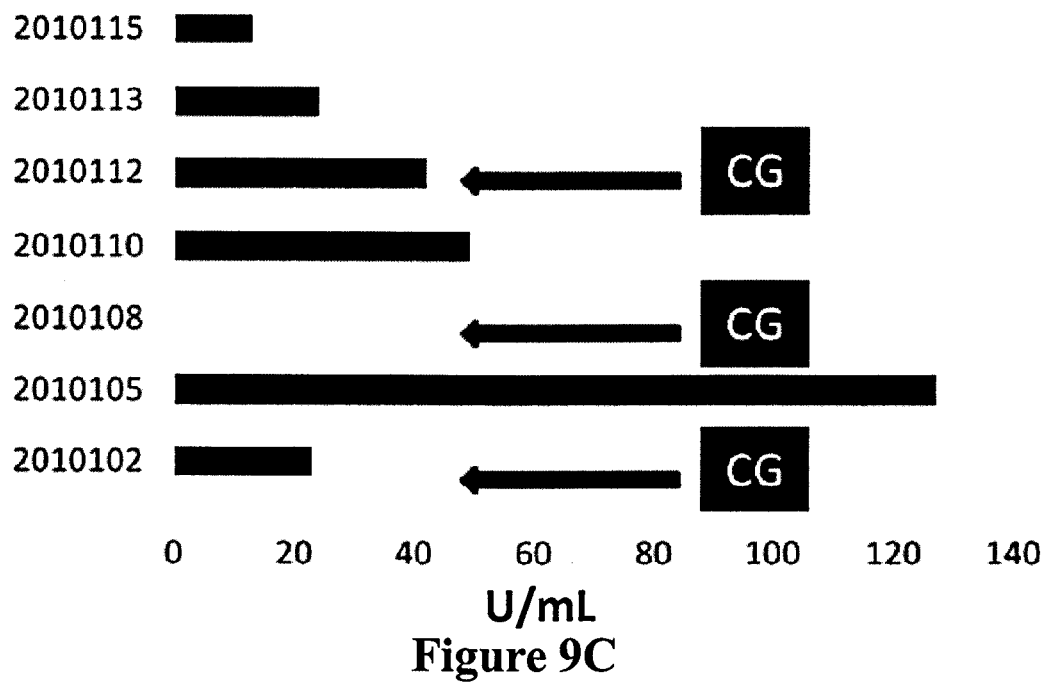
Figure 9D:
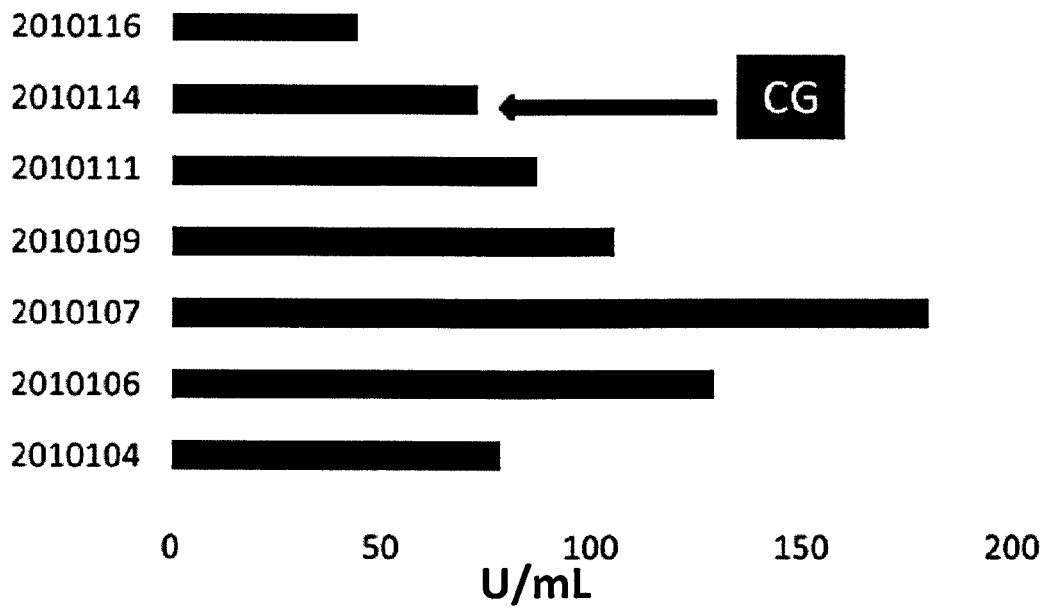
Figure 9E:
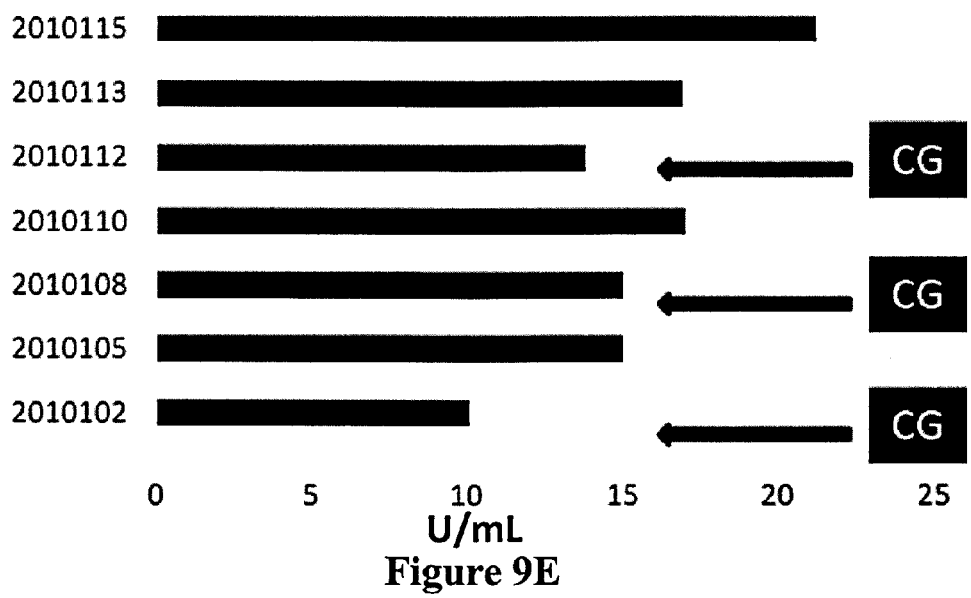
Figure 9F:
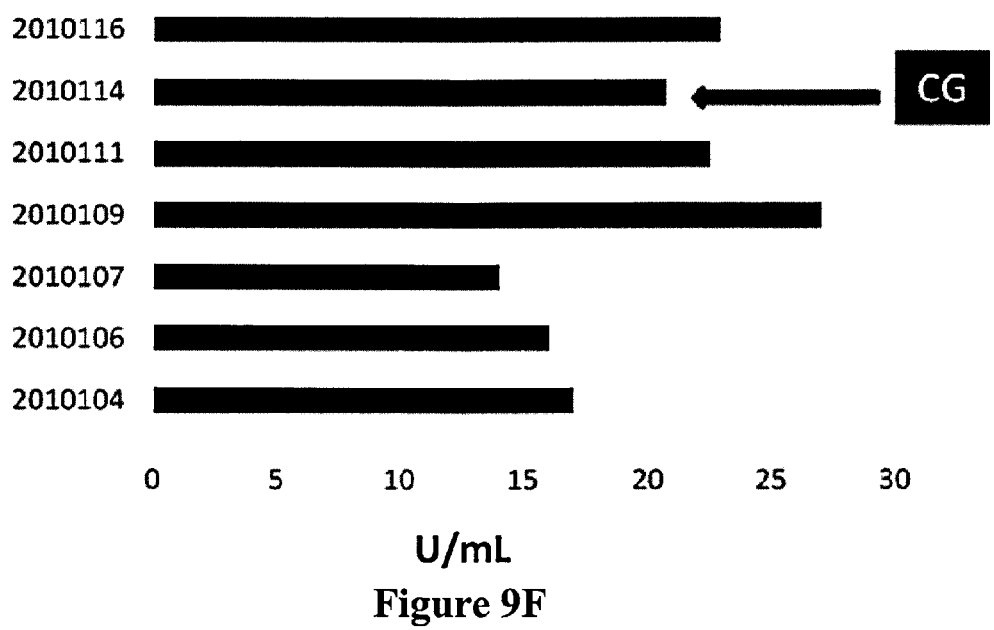
Figure 9G:
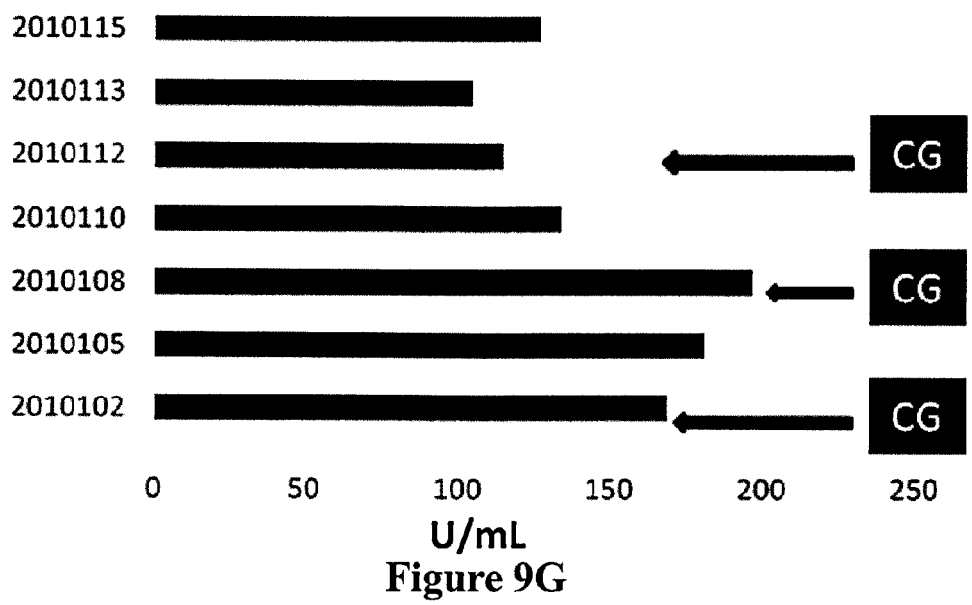
Figure 9H:
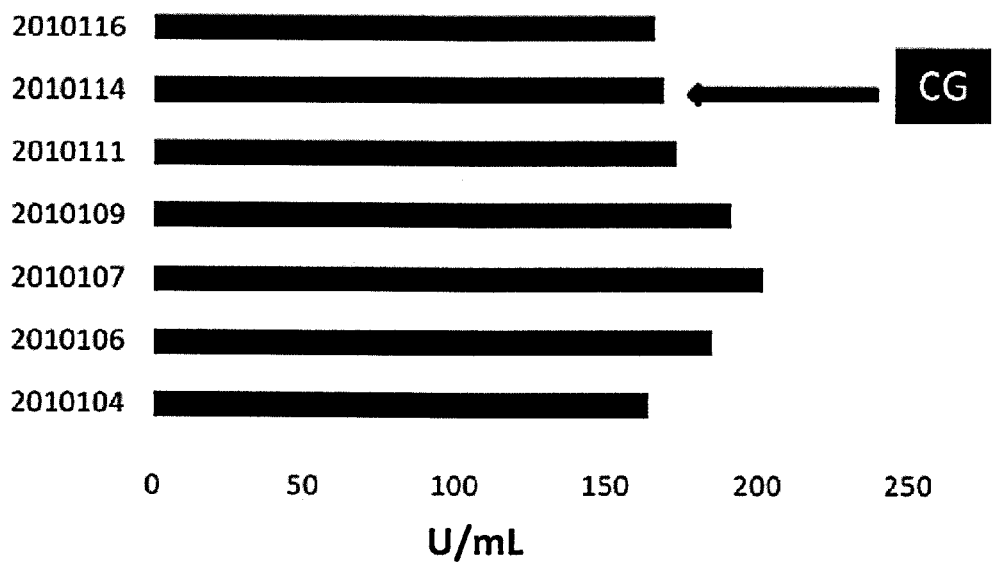

Chronic glomerulopathy (CG) is a clinical marker of AMR in a transplant patient. FIG. 6A represents normal renal tissue at six months. FIG. 6B demonstrates CG as a result of ongoing AMR. In those patients treated with placebo, 3 of 7 displayed CG, whereas, in those patients treated with Cinryze®, only 1 of 7 displayed CG. These tissue studies were confirmed by electron microscopy (EM) of obtained renal tissue (FIG. 7). FIG. 7A represents a normal EM image of renal tissue whereas FIG. 7B represents an electron micrograph of renal tissue having CG. Examining such electron micrographs, it was determined that in those patients treated with placebo as an adjunct to standard of care (plasmapheresis and/or IVIg), 3 of 7 displayed pathology consistent with CG, whereas, in those patients treated with Cinryze® as an adjunct to standard therapy, 1 of 7 displayed pathology consistent with CG.

Additionally, the day 13 C1-INH antigen levels and functional C1-INH levels in patients treated with placebo or Cinryze® were correlated to the 6 month clinical outcomes of the patients. The day 13 baseline adjusted (i.e., corrected), and unadjusted, C1-INH antigen and functional levels were first measured (FIG. 8). The data from these measurements were then graphically correlated to the 6 month clinical outcomes of the same patients (FIGS. 9A to 9H). As demonstrated in FIGS. 9A and 9B, there was a lesser incidence of CG in those patients treated with Cinryze® (FIG. 9B) as compared to those treated with placebo (FIG. 9A) where the Cinryze® patients exhibited 14% CG and the patients receiving placebo exhibited 43% CG.

At 6 months post-treatment it was also determined that those patients demonstrating low C1-INH antigenic levels at day 13 above their baseline entry levels also exhibit the presence of CG. Thus, there was an observed correlation between baseline corrected C1-INH antigen and the presence of CG in renal tissue.

Figure 10A:
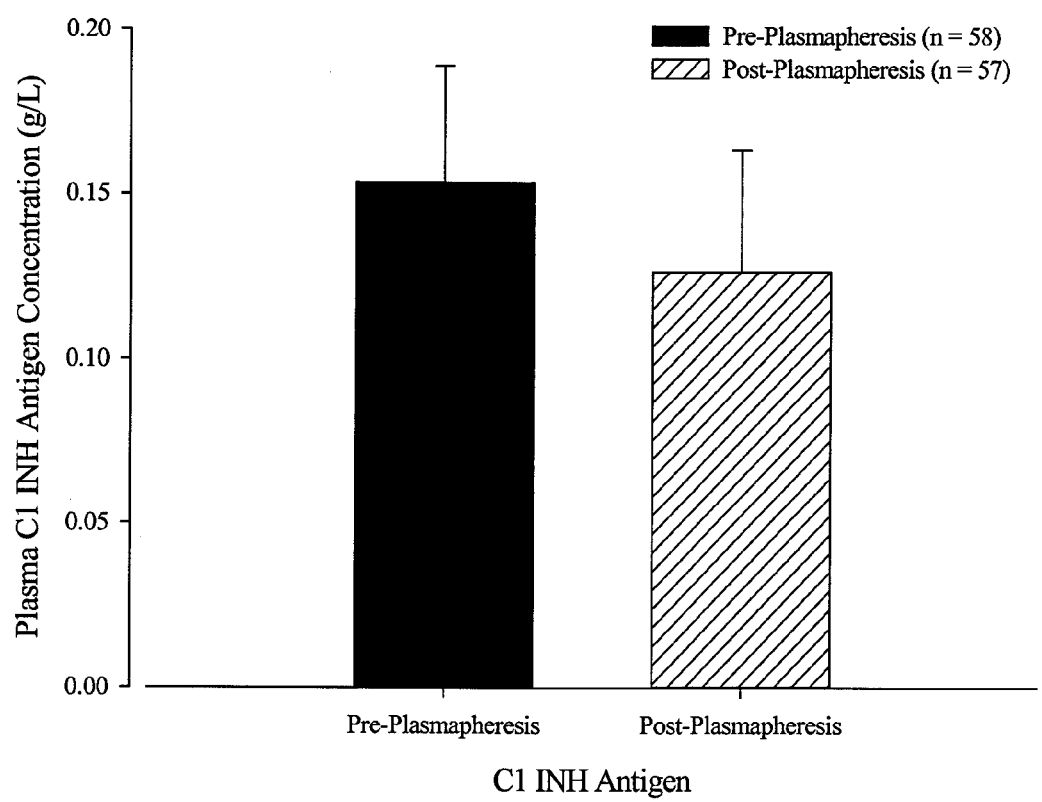
FIGS. 10A and 10B graphically illustrate the effect of plasmapheresis on serum C1-INH antigenic (FIG. 10A) and functional (FIG. 10B) levels. As demonstrated in FIGS. 10A and 10B, plasmapheresis depleted serum C1-INH antigenic and functional levels.
Figure 10B:
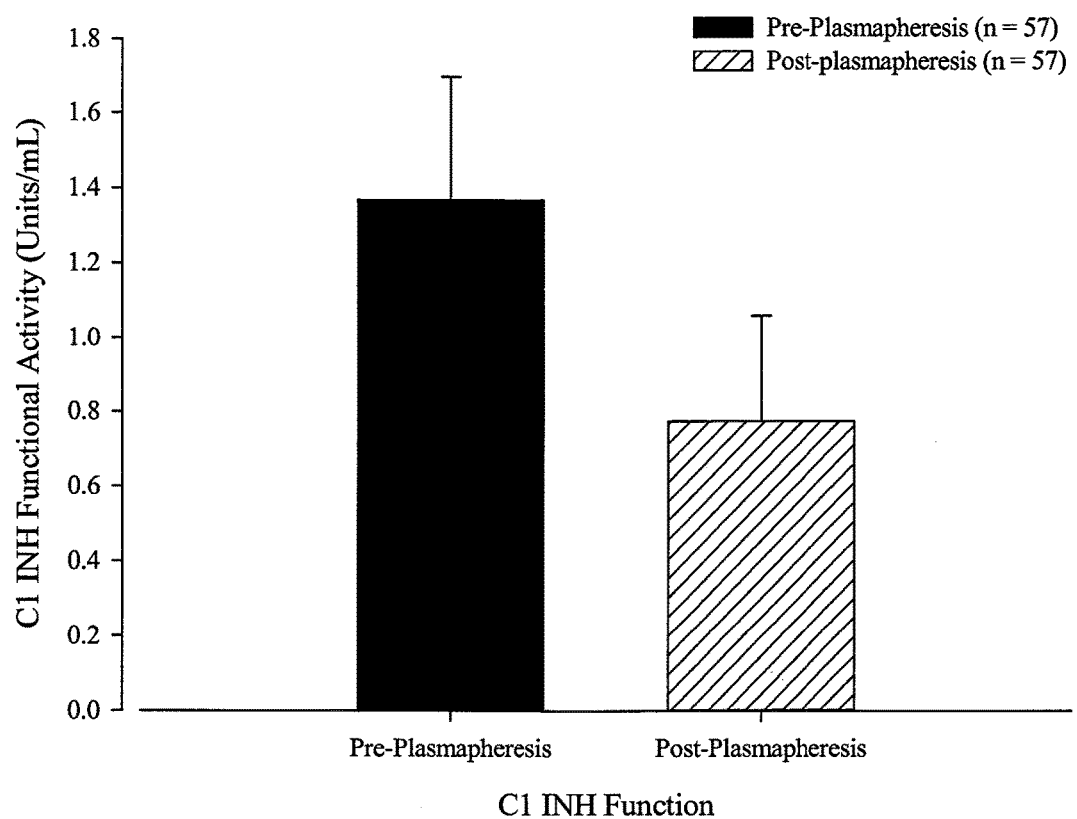

Furthermore, serum C1-INH antigenic and functional levels were depleted by plasmapheresis as demonstrated in FIGS. 10A and 10B. For instance, as shown in FIG. 10, plasmapheresis decreased both the mean C1-INH angtigenic and functional levels by 17.6% (FIG. 10A) and 43.3.% (FIG. 10B), respectively.

The present invention encompasses methods of using C1-INH (e.g., Cinryze®) as a therapy and/or add-on therapy to standard care (i.e., plasmapheresis and IVIg: both of which address donor specific antibodies) for treating and/or preventing AMR in transplant patients. An unexpected aspect of the instant invention is that early and/or short-term duration treatment with C1-INH in transplant patients results in longer term benefit after the C1-INH treatment dosing has been discontinued.

Moreover, the dosing regimen provided unexpected benefits. It is currently unknown if kidney transplant patients could ever achieve a level of C1-INH functional protein sufficient enough to effectively reduce complement activation systemically or within the transplant allograft. Indeed, the dosage of 20,000 units given in divided doses over 13 days was selected. This dose was satisfactory, not only clinically, but also in the increase of serum C1-INH functional levels above baseline.

Accordingly, the present study demonstrated that where kidney transplant patients are treated with 20,000 Units of Cinryze® over 13 days: (a) the dosage regimen was well tolerated by the kidney transplant patients; (b) such patients maintained supraphysiologic levels of C1-INH as a result of Cinryze® treatment; (c) such patients demonstrated early improvement in renal function; and (d) such patients demonstrated less glumerulopathy at 6 months with respect to placebo. Therefore, the treatment methodology tested provided long-lasting therapeutic effect against AMR as compared to the treatments currently in the field.

There are publications cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions and methods described herein that embody the present invention can, in alternate embodiments, be more specifically defined by any of the transitional terms "comprising," "consisting essentially of," and "consisting of."

What is claimed is:

1. A method of treating antibody-mediated rejection (AMR) of an organ allograft in a patient in need thereof,
the method comprising administration of a C1 esterase inhibitor (C1-INH) protein at a dose of about 20,000 units given in divided doses over a duration of about 1 to 30 days,
wherein the administration is initiated within 1 to 90 days of organ transplantation, treatment with plasmapheresis, treatment with intravenous immunoglobulin (IVIg), or diagnosis of AMR of the patient,
wherein the method results in a therapeutic effect lasting for at least 3 months after cessation of therapy.

2. The method of claim 1, further comprising subjecting the patient to plasmapheresis.

3. The method of claim 1, further comprising administering fresh frozen plasma.

4. The method of claim 1 further comprising administering intravenous immunoglobulin.

5. The method of claim 1, further comprising administering an anti-lymphocyte preparation, rituximab, bortezomib, eculizumab, or a combination thereof.

6. The method of claim 1 wherein the organ is a solid organ.

7. The method of claim 6, wherein the solid organ is selected from the group consisting of kidney, pancreas, intestine, heart, lung, and liver.

8. The method of claim 7, wherein the solid organ is a kidney.

9. The method of claim 1, wherein the C1-INH protein is plasma-derived or recombinant.

10. The method of claim 1, wherein the duration is about 10-20 days.

11. The method of claim 1, wherein the duration is 13 days.

12. The method of claim 1, wherein the therapeutic effect comprises the prevention of AMR.

13. The method of claim 1, wherein the administration is initiated within about 5 to 10 days of organ transplantation, treatment with plasmapheresis, treatment with IVIg, or diagnosis of AMR.

14. A method of treating antibody-mediated rejection (AMR) of a kidney allograft in a patient in need thereof,
the method comprising administration of a C1 esterase inhibitor (C1-INH) protein at a dose of about 20,000 units given in divided doses over a duration of about 1 to 30 days,
wherein the administration is initiated within 1 to 90 days of organ transplantation, treatment with plasmapheresis, treatment with intravenous immunoglobulin (IVIg), or diagnosis of AMR of the patient,
wherein the method results in a therapeutic effect lasting for at least 3 months after cessation of therapy.

15. The method of claim 14, wherein the C1-INH protein is plasma-derived or recombinant.

16. The method of claim 14, further comprising subjecting the patient to plasmapheresis.

17. The method of claim 14, further comprising administering fresh frozen plasma.

18. The method of claim 14, further comprising administering intravenous immunoglobulin.

19. The method of claim 14, further comprising administering an anti-lymphocyte preparation, rituximab, bortezomib, eculizumab, or a combination thereof.

20. The method of claim 14, wherein the therapeutic effect comprises improvement in renal function.

21. The method of claim 14, wherein the therapeutic effect comprises the prevention of AMR.

22. The method of claim 14, wherein the therapeutic effect comprises the treatment or prevention of chronic or transplant glomerulopathy.

23. The method of claim 14, wherein the administration is initiated within 5 to 10 days of one of organ transplantation, treatment with plasmapheresis, treatment with IVIg, or diagnosis of AMR.

24. The method of claim 14, wherein the duration is from about 10-20-days.

25. The method of claim 14, wherein the duration is 13 days.

26. The method of claim 2, further comprising administering IVIg.

27. The method of claim 16, further comprising administering IVIg.

* * * * *